United States Patent [19]

Smalling et al.

[11] Patent Number: 4,856,321

[45] Date of Patent: Aug. 15, 1989

[54] APPARATUS AND METHODS FOR MEASURING FLUID FLOW PARAMETERS

[75] Inventors: Jack W. Smalling; Leonard D. Braswell, both of Baytown, Tex.; Lawrence C. Lynnworth, Waltham, Mass.

[73] Assignee: Panametrics, Inc., Waltham, Mass.

[21] Appl. No.: 186,571

[22] Filed: Apr. 27, 1988

Related U.S. Application Data

[62] Division of Ser. No. 846,635, Apr. 1, 1986, Pat. No. 4,754,650, which is a division of Ser. No. 518,444, Jul. 29, 1983, Pat. No. 4,596,133.

[51] Int. Cl.$^4$ ............................................. G01M 3/24
[52] U.S. Cl. ................................................. 73/40.5 A
[58] Field of Search ............... 73/40.5 A, 592, 861.28, 73/40.5 R, 861.27, 597

[56] References Cited

U.S. PATENT DOCUMENTS

| | | | |
|---|---|---|---|
| 4,066,095 | 1/1978 | Massa | 73/40.7 |
| 4,515,021 | 5/1985 | Wallace et al. | 73/861.27 |
| 4,596,133 | 6/1986 | Smalling et al. | 73/24 |
| 4,754,650 | 7/1988 | Smalling et al. | 73/861.28 |

FOREIGN PATENT DOCUMENTS 1315294 5/1973 United Kingdom .
1338436 11/1973 United Kingdom .

Primary Examiner—Hezron E. Williams
Attorney, Agent, or Firm—Lahive & Cockfield

[57] ABSTRACT

An apparatus and method for measuring fluid flow parameters operate under conditions wherein the composition of the fluid flow can change rapidly thereby changing the speed of sound within the fluid and wherein the actual flow rate can change rapidly thereby further changing the transit time of acoustic energy traversing an interrogation path within the fluid. The apparatus determines the speed of sound in the fluid and the fluid flow velocity by measuring an upstream and a downstream transit time of acoustic energy within the fluid. The fluid is typically flowing within a conduit, and the transducers for transmitting and receiving the acoustic energy are precisely and carefully installed in the conduit. The measurements also allow an estimate to be made of the average molecular weight of gases passing through the conduit and hence of the mass flow rate of a gas. The measurements are taken at a frequency sufficient to satisfy the Nyquist criterion with regard to the maximum frequencies of interest for the fluid flow parameters being measured. Special techniques are developed for enabling transducer placement in preexisting conduit arrangements wherein access to the conduit is limited.

9 Claims, 12 Drawing Sheets

DIAGONAL (45 DEGREES)

MID-RADIUS (63.435 DEGREES)

45-90

MID-RADIUS-90

90-90 MID-RADIUS (BIAS)

60 PIPE RACK

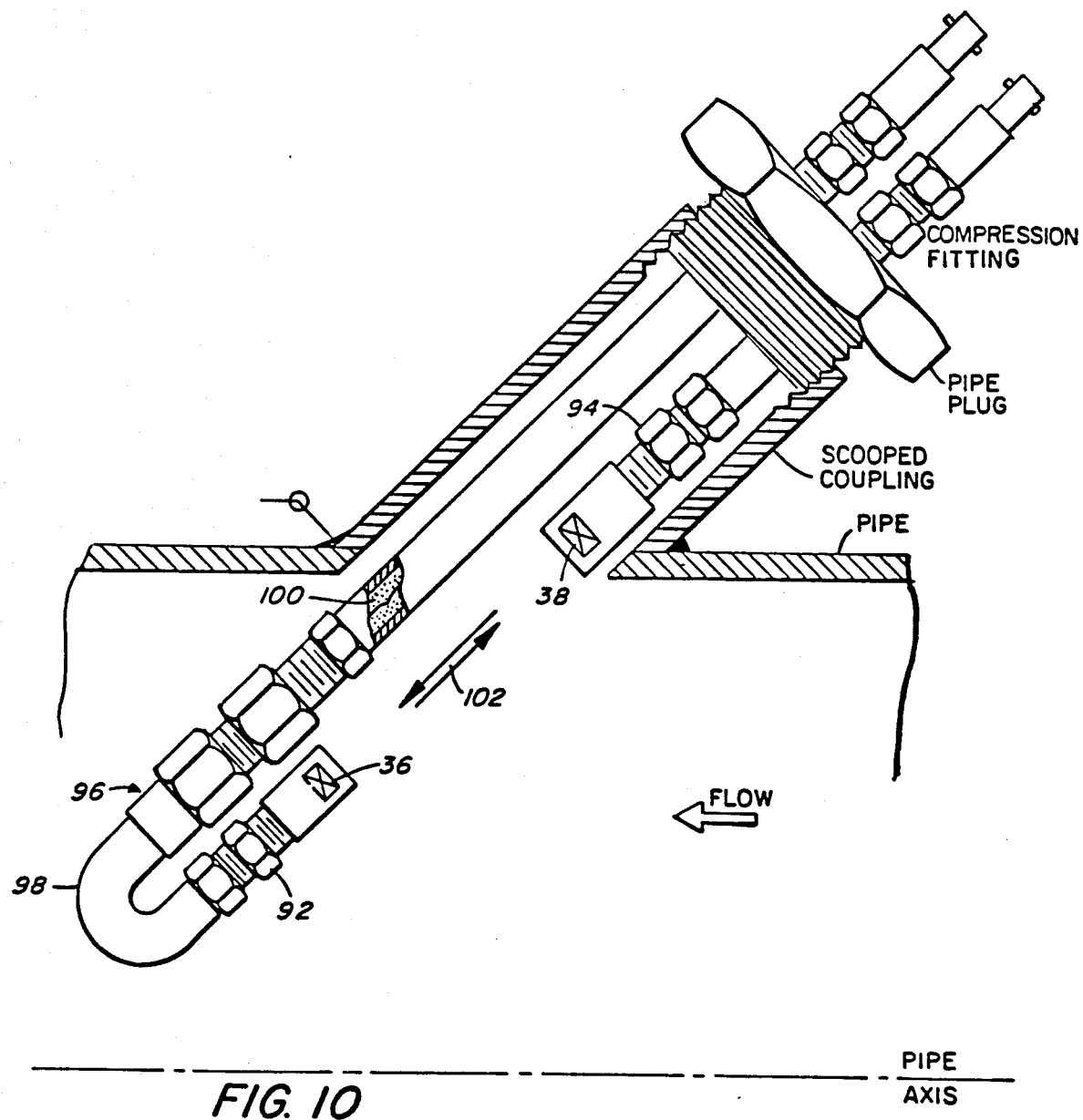
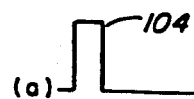
FIG. 10
FIG. 11
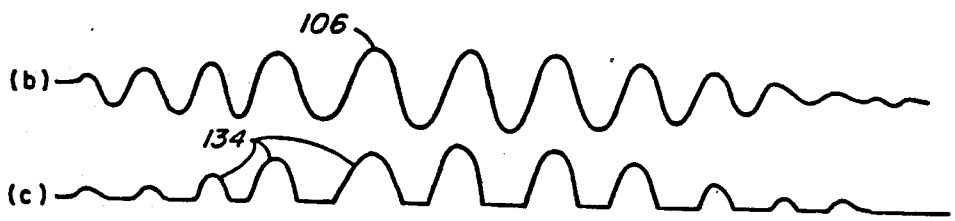

APPARATUS AND METHODS FOR MEASURING FLUID FLOW PARAMETERS

This is a division of application Ser. No. 846,635, filed Apr. 1, 1986, which is a divisional of U.S. Ser. No. 518,444 filed July 29, 1983 issued June 24, 1986 U.S. Pat. No. 4,596,133.

This invention relates generally to measuring fluid characteristics and fluid- and flow-related parameters in a conduit and more particularly to methods and apparatus for measuring fluid charcteristics and fluid flow-related parameters which vary unpredictably over wide ranges of value and in a malevolent environment hostile to instrumentation.

CROSS REFERENCE TO RELATED APPLICATIONS

This application is related to Lynnworth and Matson, U.S. application Ser. No. 518,344 now U.S. Pat. No. 4,596,133, filed 29 July 1983, and entitled "Integrated Threshold Arming Method and Apparatus", and to Wallace et al, U.S. application Ser. No. 518,738 now U.S. Pat. No. 4,515,021, filed 29 July 1983, and entitled "Improved Intervalometer Time Measurement Apparatus and Method". Those cases describe various electrical methods and apparatus particularly useful in implementing the invention disclosed herein. To the extent they are not already described in this application, U.S. Ser. Nos. 518,344 and 518,738 are incorporated herein by reference.

BACKGROUND OF THE INVENTION

Many fluid flow applications require that measurement and analysis of the fluid flow and other fluid characteristics be performed under adverse conditions. Consider, for example, the petroleum industry, where protection against overpressure of facilities such as vessels, piping, and machinery, etc., is provided by the use of safety valves at the various processing stations. The discharges from these stations are collected in headers and are directed from there into a main large discharge conduit. Typically, single headers collect discharges from a small number of safety valves, for example ten to twenty. A plurality of these single headers can be collected into a large collection header for an entire manufacturing unit. The gases are burned at an ignited flare or burner pit and from there are vented safely to the atmosphere.

At any particular time, many of the safety valves may be leaking. Usually, however, the leakage rate from any one valve is very small and of no great concern. At times, however, the valves may leak excessively, for example from operation at a pressure too slose to the safety valve setting, from mechanical damage during an overpressure incident, or from deterioration due to corrosion, erosion, fouling, or some other cause. Leakage from a safety valve can be costly due to the loss of a valuable product, degradation of the product being manufactured, or by creating problems from operation of the flare system. Furthermore, unless monitored, the leakage might not be corrected for an intolerably long period of time.

There have been many attempts to detect leakage in the collection headers. These previous methods have not proved successful. The malevolent atmosphere in the flare headers is one of the principal reasons. Thus, because the flare stack receives material from many sources, the process conditions are very hostile to instrumentation. Commonly, there can be fouling, corrosion, precipitation of solids, precipitation of high molecular weight polymers, and over the passage of time, various combinations of these conditions. Thus, for example, turbine meters have been employed but have proved inadequate due to clogging of their moving parts. Also, most ordinary engineering materials fail due to corrosion. Further, the impact resulting from sudden pressure surges, temperature transients, steam, long distances from sensors to electronics, vibration, etc., all combine, as noted above, to present an unfavorable environment which renders inoperable prior measurement systems. Furthermore, flow detection methods for leakage detection using differential pressure instruments are ruled out by the safety system back-pressure considerations which forbid pressure increases in the flare headers. In addition, the flow conditions within the header include both positive and negative directions of flow. The instrument systems noted above do not distinguish flow direction nor do they compensate for negative flow.

A further consideration in connection with measuring flare stack flow is the location of and limited access to existing pipes and the inability to take a particular pipe out of service merely to install the flowmeter. This means that it is important to be able to retrofit instruments such as flowmeters to an existing facility using, for example, an on-line hot tap procedure. Furthermore, the hot tap must be positioned exceptionally accurately so that subsequent fluid interrogation occurs along a predetermined path, for example at 45° to the pipe axis, on a tilted diameter, or along a chord segment or in the axial direction at a prescribed distance from the pipe wall, etc., so that the sampled portion of the flow profile bears a calculable and/or reproducible relationship with the area averaged flow velocity.

In addition to the hostile environment presented by the flare stack headers, there is a further difficulty, even if instrumentation can be provided to withstand the hostile environment, that the gas flow characteristics within the header can change rapidly with time for a variety of reasons. Thus, the typical applications of ultrasonic flow measurement, such as that described in Lynnworth U.S. Pat. Nos. 4,103,551 and 3,575,050, are not directly applicable. In those references, it is generally assumed that the flow rate is relatively constant with time; that the fluid characteristics do not change violently; and that the composition and/or sound speed of the medium passing through the pipe is not only known, but constant, at least for intervals comparable to the measuring instrument response time. It is also frequently assumed that adjacent or neighboring fluid elements have substantially identical fluid characteristics so that crossed interrogation paths can be employed.

It is also often assumed that the received amplitude from measurements made upstream and downstream will be identical in amplitude. It has been shown however that the amplitude often differs depending upon whether the interrogation path is directed upstream or downstream. See for example Ingard, U. and Singhal, V. K., *Journal of the Acoustical Society of America*, Vol. 60, pp. 1213–1215, 1976.

It is therefore a primary object of the invention to reliably and accurately measure various characteristics of a flowing fluid particularly under adverse conditions such as the flow conditions in a collection header or in a main flare line. Other objects of the invention are the accurate measurement of fluid flow in spite of differences between the amplitude and/or shape of pulses transmitted downstream versus upstream, and despite density, pressure and turbulence variations, composition variations, and sound speed and flow rates which change quickly with time. Further objects of the invention are providing a measure of mass flow rate, fluid flow velocity, identification of the source of a leak, and installing flow measurement apparatus in a conduit with high accuracy and reliability of placement despite access restrictions.

SUMMARY OF THE INVENTION

The invention relates to methods and apparatus for measuring characteristics of fluids, particularly the flow rate and sound speed thereof. Many fluid streams unexpectedly exhibit rapid or high frequency changes in flow rate and composition. The invention provides measurement techniques which accomodate rapid fluctuations in flow rate or fluid composition (as opposed to a steady state conditions) without loss of accuracy.

The invention is particularly useful for measuring gas streams having low concentrations of key components at a variety of flow rates including the range of from zero to 50 feet per second. At very low flow rates, for example, zero to one ft/second, the apparatus and method of the invention are particularly suitable and useful. At such low flow rates, in a malevolent environment such as the flare stack, the invention is particularly noteworthy, since it has not hitherto been possible to accurately and practically measure such quantities, even under steady state conditions, with ordinary (non-acoustic) flowmeters, because those flowmeters that have the high velocity range are too insensitive at the low end of their range. Prior acoustic flowmeters are not immediately adaptable to this class of application. In addition, under the much more adverse circumstances of rapid fluctuations, pressure dropping devices, such as orifice plates, do not respond linearly.

In particular, the invention is described in connection with an apparatus and method for detection and analysis of leaks in a flare stack system. The flare stack system has a plurality of processing stations, each processing station having associated therewith a safety discharge conduit and a safety discharge valve. The safety discharge valve is connected to control discharges from the processing station to the conduit. A header conduit connects to a plurality of the discharge conduits. The detection apparatus features a first transducer mounted at a first location in the header conduit, and a second transducer mounted at a second location in the header conduit, the first and second transducers defining therebetween an interrogation path. Circuitry is provided for exciting the first and second transducers, preferably in serial alternation as described hereinafter, to emit acoustic energy. The circuitry further measures an upstream transit time and a downstream transmit time for the propagation of energy between the first and second transducers in the upstream and downstream directions respectively. The excitation and measuring operations are repeated to generate transit time measurements at a rate greater than at least ten times per second and circuitry is further provided for determining from the transit times the speed of sound in the fluid as a function of time and the fluid flow velocity as a function of time. Thereby a gas leak through the safety valves can be detected.

The leak detection apparatus further features determining from the speed of sound in the fluid, an average molecular weight of the fluid as a function of time. This can be employed for identifying the particular process station at which the leak occurred.

The leak detection apparatus further features repeating the excitation and measuring operations at a frequency which satisfies the Nyquist criterion; that is, at a frequency greater than two times the highest frequency of significance of the expected sound speed fluctuation and the expected fluid velocity fluctuation. By sampling the fluid often enough, the apparatus and method provides an accurate measure of the time-average flow velocity. This is in contrast to orifice plates, venturies, and other pressure dropping sensors which generally yield the root-mean-square (rms) value of the flow. The rms value can be significantly higher than the true time average value for flows with a significant unsteady component.

In another aspect, the invention relates to a method for installing the transducers in the header conduit walls. According to the method, which employs a hot tapping procedure for installing the transducers without taking the headers out of service, there is featured the steps of marking by a physical indentation or scribed intersection point, a location on the conduit outside wall at which a transudcer is to be installed, using that indentation or intersection point to position a starting structure on the outside wall, and welding the structure to the wall. Thereafter the machining or hot tapping procedure is performed for cutting an aperture in the side wall using the starting structure as a guide. The transducer is then mounted at the prepared located in the conduit wall or along the axis or path defined by the indentations or scribed intersection points.

The marking step can employ center punching or drilling the outside conduit wall and providing in the starting block a location hole for positioning the starting block relative to the indentation. Positioning can be accomplished by passing a pointed locating shaft through the location hold in the starting structure relative to the indentation. Preferably, the starting structure has been contoured at its bottom to match the contour of the outside wall.

In another aspect, a template overlay, for example mylar, is employed for marking the indentation location and for scribing match lines on the conduit outside wall. The overlay's layout can compensate for the thickness of the overlay if the markings are on the outside surface of the template overlay, when it is wrapped around the conduit. The method further features positioning the starting structure using both the indentation and the scribed lines. According to this method, a jig and stub assembly is bolted to the welded starting structure after which the stub assembly is welded to the conduit. The jig is thereafter removed and a valve is bolted to the stub. The standard hot tapping process then takes place.

In other aspects of the invention, the preexisting flare stack facility generally provides highly restricted access to the header conduits. Consequently, several new methods are employed for inserting the transducers at appropriate locations within the conduit structure for providing the upstream and downstream transit times. In one aspect, the apparatus provides for mounting the transducers through a single opening in the conduit. According to this apparatus, the mounting system provides for acoustically isolating the upstream and downstream transducers. Furthermore, when the path is a tilted radius, in either a one-port or a two-port interrogation system, it is recognized that, apart from the perturbing effects of the transducers and their supports, the meter factor (defined in more detail below) is the same as for a tilted diameter path, that is, 0.7500 for laminar flow and a known function of the Reynolds number for turbulent flow.

When the upstream and downstream transducers are provided through separate access openings in the conduit, the restricted nature of the facility may require that a chordal segment of the conduit be employed. The chordal segment may also be employed for example where a full diameter or full chord proves to be too long and provides excessive attenuation for the pulsed signals. In yet another mounting configuration, the interrogation path may include a reflection off the conduit interior wall for providing an elongated interrogation path between the transducers. In this application, one or more reflection elements are advantageously mounted at the conduit wall for providing better reflective characteristics thereby reducing the attenuation or scattering associated with the reflected pulse and further reducing diffusion of the signal. In a preferred embodiment, the reflecting elements can project into the interior of the conduit to aid self-cleaning of the reflectors.

While the description herein is particularly directed to the flare stack gas application of the apparatus and method, there exist many other fluid applications to which the invention is particularly suited. These corresponding or analogous applications can be in such diverse fields as medicine, biology, the automotive industry, aerospace, military applications, oceanography, meteorology, cryogenics, etc. One common denominator in all of these applications, be they for gases or liquids, is the typical or potential occurrence of rapidly changing sound speed, fluid velocity, attenuation of the signal, and/or characteristic acoustic impedance of the fluid.

In some medical or biological applications, phenomena as elementary as breathing have an unsteady and bidirectional flow with variable temperature, gas composition and humidity levels. A surge, for example a cough or hiccup, illustrates the transient flow and a response to physical exertion may include combinations of ramp-like and oscillatory respiratory and blood flow. In oceanography and meteorology, phenomena such as mixing of streams, wind gusts, the effect of rain or snow on wind, etc., are applications to which the present invention is applicable. Further, in some cryogenic flow processes, two liquids of different densities and different sound speeds mix, giving rise to unsteady or variable sound speed which is independent of flow velocity.

The invention is further advantageous with respect to what is presumed to be steady flow applications of a substantially invariant and mild fluid, for example water at room temperature, where the application includes the risk of occasional unsteady flow due to inadvertent changes of, for example, a valve setting, failure of a control element, accidental thermal input, etc. Thus, portions of the present invention are applicable to certain filling operations wherein most of the fill cycle occurs at a fixed rate (that is, the fluid flow rate is constant) but where the end of the fill cycle occurs at a slower rate and may include flow velocity transients as the operator or control system attempts to "top off" the container. At lower flow rates, thermal inputs or heat transfer are more likely to influence the sound speed than at the higher flow rate.

In some aerospace and high performance engine applications, high pumping rates can cause the liquid fuel to heat up so that the sound speed is not constant but instead, can decrease at a rate that depends on the time and temperature history of the liquid. Since the temperature coefficient of the sound speed is typically a few meters per second per degree Celsius, for example minus four meters per second per degree Celsius, it is clear that a small but steady change in the temperature can lead to errors in the fluid flow velocity calculations if those calculations erroneously assume that the speed of sound is constant. Thus, if the speed of sound differs by only one meter per second between the upstream and downstream interrogations, there could result a misinterpretation of the received data, that is, the change of sound speed can be erroneously interpreted as a change in flow velocity.

BRIEF DESCRIPTION OF THE DRAWINGS

Other objects, features, and advantages of the invention will appear from the following description of a preferred embodiment taken together with the drawings in which:

FIG. 10 shows a preferred embodiment of an insertable ultrasonic structure in accordance with the invention;

FIG. 11 is a display of transmitted, received, and rectified signals useful in explaining the invention;

DESCRIPTION OF A PREFERRED EMBODIMENT

Figure 1:
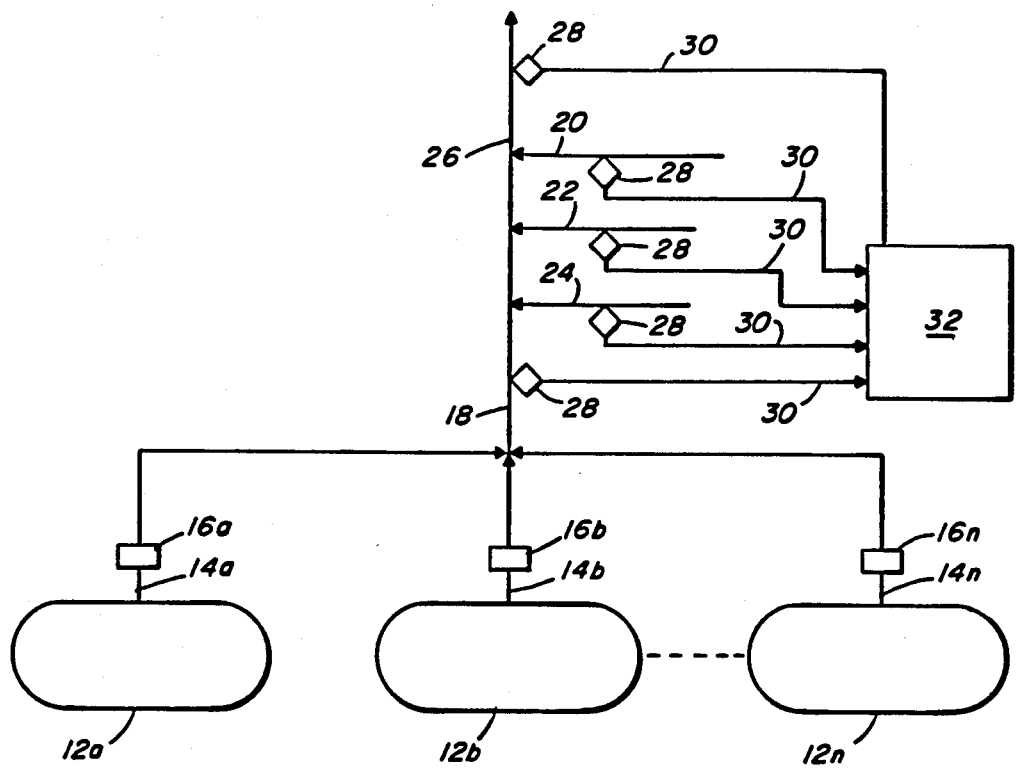
FIG. 1 is a schematic representation of a typical refining application in which the invention is particularly useful.

Referring to FIG. 1, a petroleum manufacturing facility has a plurality of process stations 12a, 12b, ..., 12n wherein different manufacturing processes, or process stages, can be performed. Typically, these manufacturing stages are interconnected to form a complete manufacturing process by piping and control connections (not shown). Each of the process stages further includes a single discharge conduit 14a, 14b, ..., 14n having associated therewith a safety valve 16a, 16b, ..., 16n respectively. The discharges from these stations are collected in a single header 18 which typically has between ten and twenty safety valves and related conduits connected thereto. Further, single headers 20, 22, and 24 from other manufacturing stations can be collected into increasingly larger headers until all of the discharges from an entire manufacturing process can be collected into a single large header 26. The gases from header 26 can be ignited and burned in an elevated flare or burner pit and from there can be safely vented to the environment.

In accordance with this embodiment of the invention, one or more of the safety valves 16a, 16b, ..., 16n may leak and generally the leakage rate is small and of no great concern. At other times, however, the valves may leak excessively for one of many reasons, resulting in substantial flow through the various headers. The quantity of flow through the header as well as its content can be an important parameter in determining the efficiency of the manufacturing process as well as the safety and efficiency of the flare system. Consequently, it is desirable for each header to determine the quantity of flow and, if possible, the content of the gases passing through the conduits. In this respect therefore, according to the invention, a gas flow velocity measurement and analysis system is employed for determining the gas flow rate through the conduits as well as mass flow rate. Thus, each header has secured thereto a flow measurement transducer apparatus 28, the flow measurement apparatus being connected via cables 30 to a microprocessor controlled measurement analysis determination apparatus 32.

Figure 2:
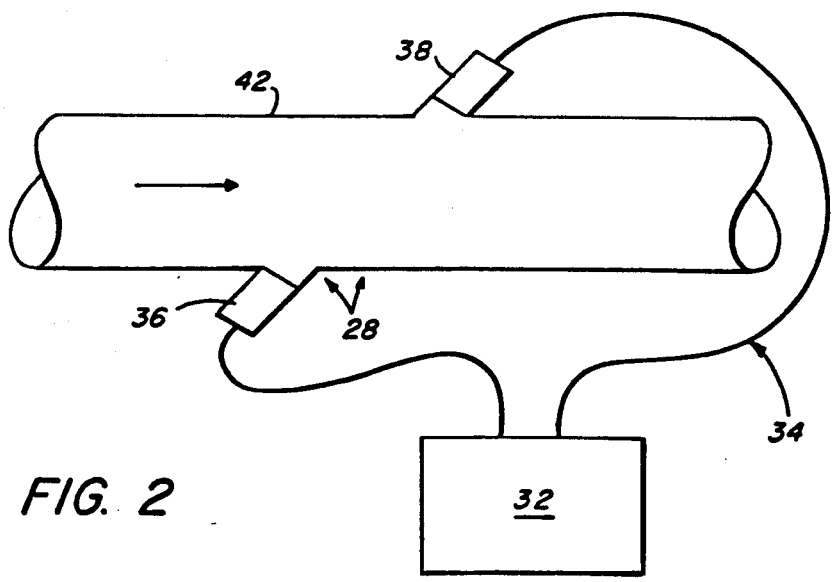
FIG. 2 is a simplified schematic representation of the upstream and downstream acoustic interrogation apparatus.

Referring to FIG. 2 an acoustic flowmeter 34, including the analysis and measurement apparatus 32 and the measuring system 28, uses an upstream transducer 36 and a downstream transducer 38 to transmit under control of measurement apparatus 32 an ultrasonic energy pulse upstream and downstream through a fluid 40 in a conduit or pipe header 42. As is well known, two measurements are required for determining the velocity of the fluid. The first measurement requires an acoustic signal (the ultrasonic energy pulse) to be sent upstream from transducer 38 to transducer 36 and that the transit time, T1, be measured. The acoustic signal is then sent in the opposite, downstream direction, and the downstream transit time, T2, for this traversal of the path between the transducers, is measured. From these two measurements, the sound velocity, C, of the signal in the medium, the flow velocity, V, of the gas in the conduit, and, as will be described below, mass flow rate MV, can be determined.

As is well described in literature, the velocity of sound in the medium, C, is calculated according to Equation 1:

$$C = T/D \qquad \text{(Eq. 1)}$$

where $T = (T1+T2)/2$, is the average transit time, and D is the fluid path or distance between the transducers. (Strictly speaking, $T = (T1+T2-2TW)/2$ where TW equals all delays not in the fluid itself.)

Further, as is well known, the flow velocity V is proportional to $C^2 dt/2D$ where dt equals the difference in recorded tansit times, that is, $dt = T1 - T2$.

Applicants have further discovered that at a given temperature, the speed of sound in a gas, C, is indicative of the aveage molecular weight of the gas, for gases in which the specific heat ratio is not independent of molecular weight. The molecular weight correlation has been confirmed for a class of generally parafinic hydrocarbons that in normal operation are found in the flare system. The available data further suggests that it is possible that a similar correlation exists for olefins and di-olefins. Furthermore, experimental data relating to catalytic cracking gas indicates that the correlation between the speed of sound and molecular weight is useful for aromatic products, at known temperatures. Hence, a determination of mass flow rate to an accuracy on the order of one percent, based on acoustic measurements of the speed of sound and velocity of a fluid, together with temperature and pressure information, can be obtained by the heretofore unknown correlation between the speed of sound in a fluid and molecular weight, for at least several gas compositions. The sound velocity measurement, then, together with the flow velocity, produces a measurement of mass flow rate by calculations which involve well known equations.

MASS FLOW RATE MEASUREMENT

Figure 3:
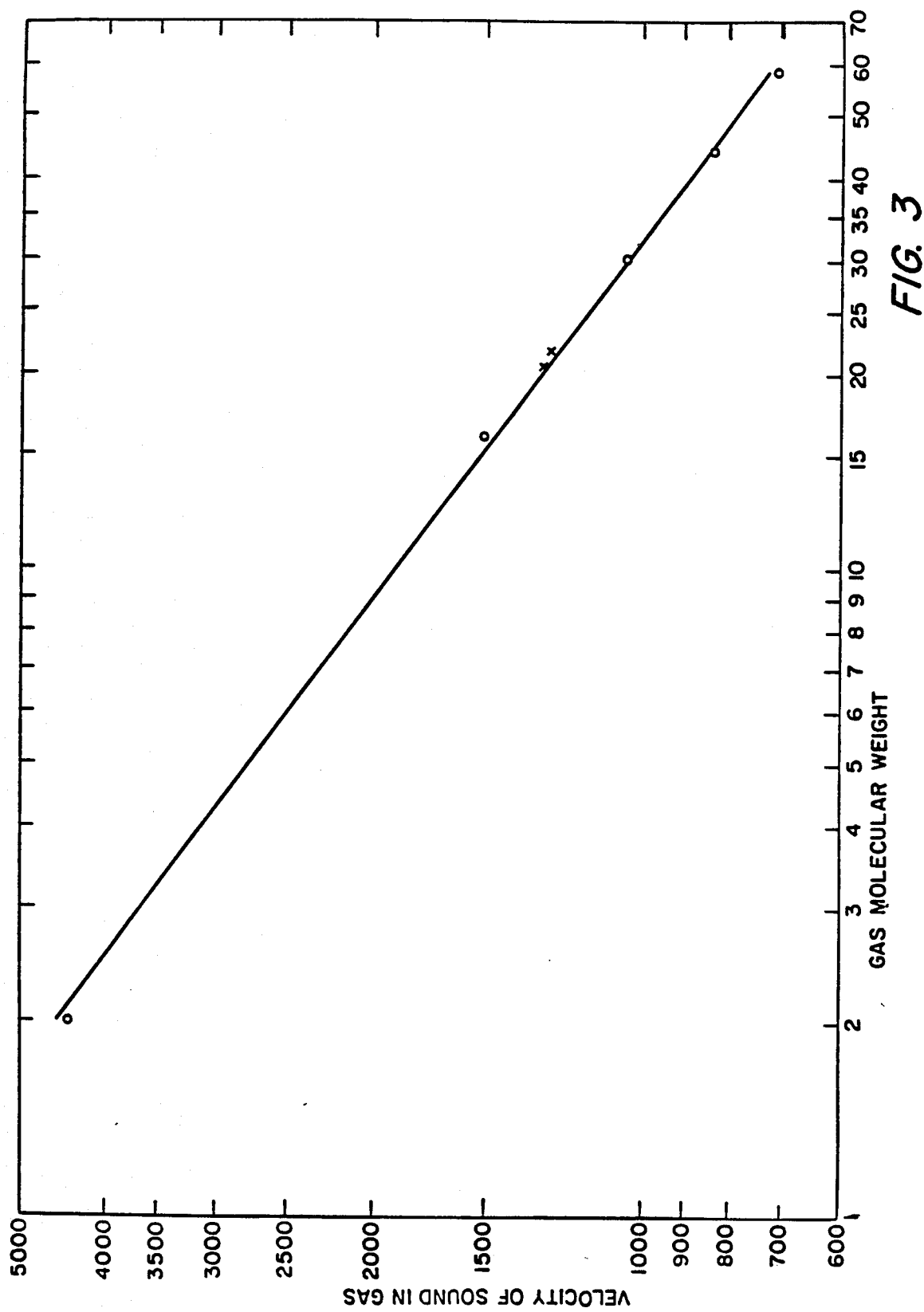
FIG. 3 is an illustration of the relationship between the speed of sound in a gas and the gas molecular weight.

From experimental data comparing the speed of sound in the gas, at a given temperature and pressure, and for several hydrocarbon gas mixtures, it is possible to correlate sound velocity and molecular weight. Referring to FIG. 3, one equation which approximates the experimental relationship illustrated there (for a molecular weight in the range of about 70) is:

$$MW = \text{Antilog}\,(7.012 - 1.836[\log C]) \qquad \text{(Equation 2)}$$

where MW is the molecular weight of the gas in lb/mole and C is the speed of sound in the gas in ft/sec.

Figure 4:
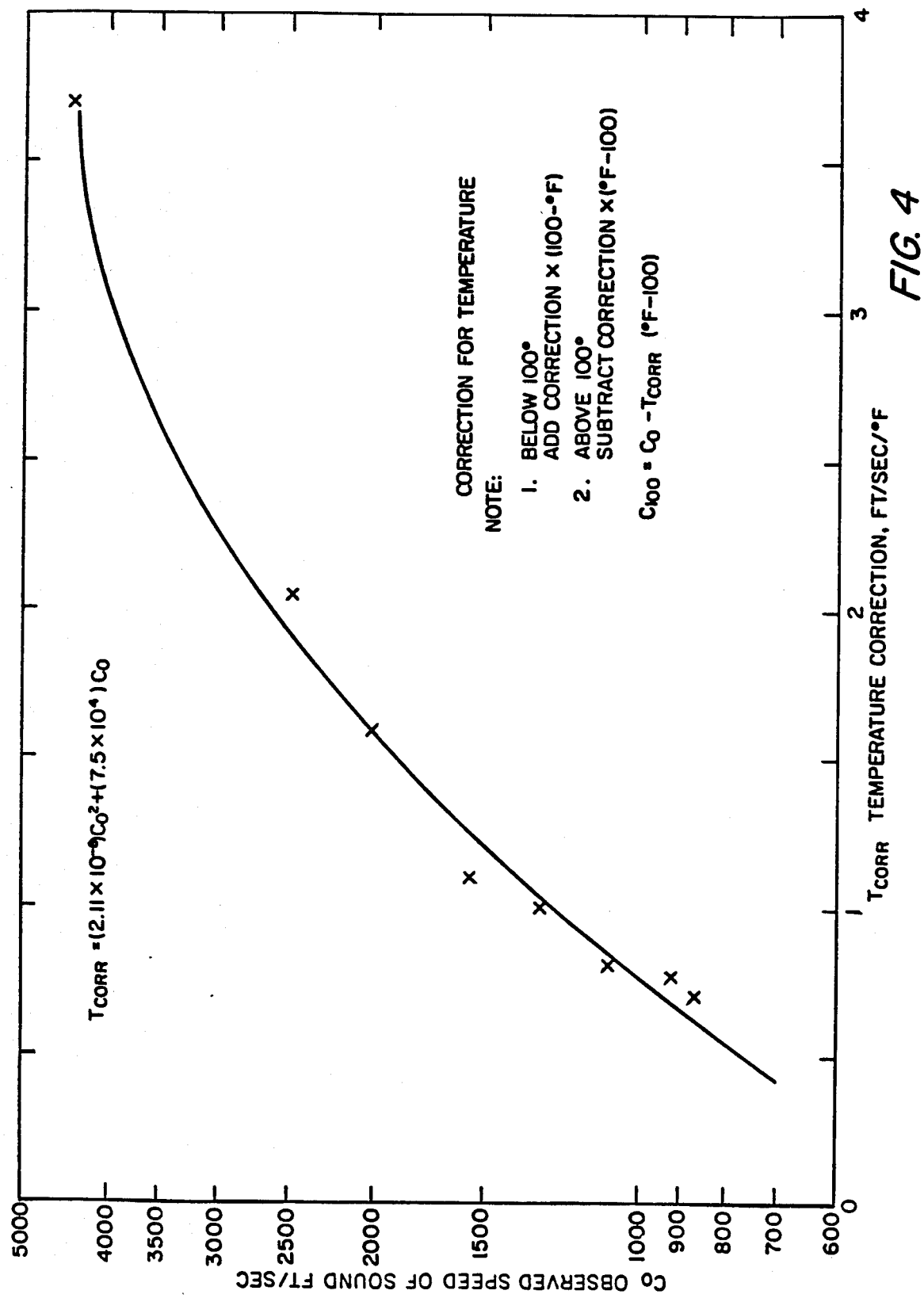
FIG. 4 is a graph illustrating the relationship of the speed of sound in a gas and the temperature correction factor for the gas.

Since sound speed varies with temperature, it is possible to measure different sound speeds for a gas at different temperatures. One set of data typical of flare gas hydrocarbon mixtures is presented in FIG. 4. In order to use the molecular weight correlation of Equation 2, it is desirable to correct for temperature. An approximation to the graph of FIG. 4 is:

$$T_c = (2.11 \times 10^{-8})C_o^2 + (7.5 \times 10^{-4})C_o \qquad \text{(Equation 3)}$$

$$C_{100} = C_o - T_c\,(T_o - 100) \qquad \text{(Equation 4)}$$

where $T_c$ = temperature coefficient of sound speed;
$C_o$ = speed of sound observed, fps;
$T_o$ = temperature of gas; and $C_{100}$ = speed of sound at 100° F., fps.

Then the mass flow can be calculated by the following equation:

$$M = V_o \times \frac{MW}{359} \times \frac{460 + 32}{460 + T_o} \times \frac{P_o}{14.7} \times D^2 \times \frac{\pi}{4} \times 3{,}600 \quad \text{(Equation 5)}$$

where
M = mass flow rate;
$V_o$ = observed velocity, fps; and
$P_o$ = observed pressure, psia Combining Equations 3 and 4, $$C_c = C_o - [(2.11 \times 10^{-8})C_o^2 + (7.5 \times 10^{-4})C_o](T_o - 100) \quad \text{(Equation 6)}$$

Simplifying and combining Equations 2, 3, 4, and 6:

$$MW = 10^{7.012}/C_c \quad \text{(Equation 7)}$$

Approximating equation (7) by a power series, $$C_c 1.836 = 637.194 \left[ 1 - 1.836 \left( \frac{1{,}450 - C_c}{1{,}450} \right) + 0.767448 \left( \frac{1{,}450 - C_c}{1{,}450} \right)^2 + 0.041954 \left( \frac{1{,}450 - C_c}{1{,}450} \right)^3 + 0.012213 \left( \frac{1{,}450 - C_c}{1{,}450} \right)^4 \right] \quad \text{(Equation 8)}$$

Then Equation 5 can be rewritten as:

$$M = V_o \times \frac{10^{7.012}}{C_c 1.836} \times \frac{1}{359} \times \frac{492}{460 + T_o} \times \frac{P_o}{14.7} \times D^2 \times \frac{\pi}{4} \times 3{,}600 \quad \text{(Equation 9)}$$

The empirical results presented hereinabove, relating sound speed C and observed temperature $T_o$ to the molecular weight MW and hence mass flow rate M of the gas in the flare stack header begins with the well known gas equation which holds $PV^\gamma$ = constant and $$PV = RT \text{ or } P = \rho RT \quad \text{(Equation 10)}$$

where P is the absolute gas pressure; V(= 1/$\rho$) is the specific gas volume; $\gamma = C_p/C_v$ is the specific heat ratio of an ideal gas; R is the universal gas constant; and T is the absolute gas temperature.

It is also well known that the speed of sound in a gas, C, can be calculated from:

$$C = (\gamma RT/MW)^{\frac{1}{2}} \quad \text{(Equation 11)}$$

where MW is the average molecular weight of the gas. Generally, gamma ranges from about 1.0 to 1.67. Thus, by arbitrarily picking gamma equal to 1.33, one can always calculate the average molecular weight of the gas to within an accuracy of about 33%. The empirical correlation noted above enables one to improve the accuracy of the average molecular weight determination to one or two percent.

Figure 5:
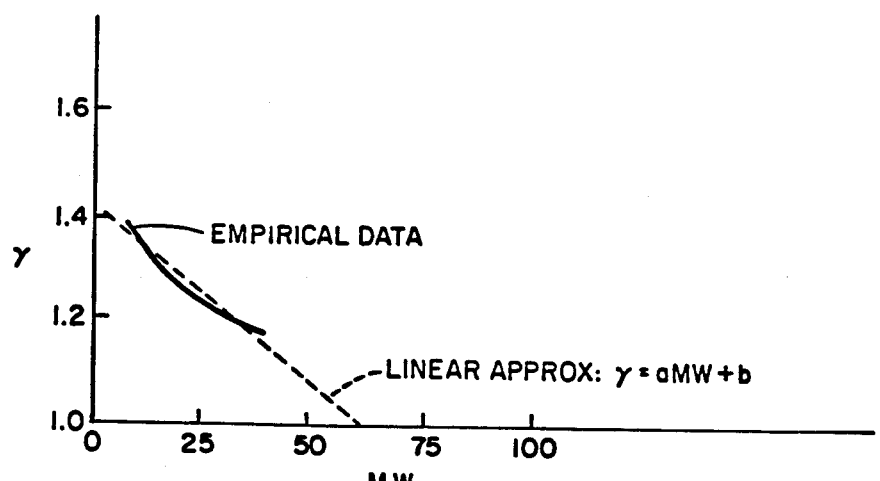
FIG. 5 is a graph representing the approximation by a straight line of the empirical data relating gamma and molecular weight.

Stated another way, where greater accuracy is required, Equation 11 requires that gamma be known. On the other hand, the gases present in the headers 18, 20, 22, 24 are unknown and hence from Equation 11, the calculation of molecular weight appears to be a function of both the speed of sound in the gas and the specific heat ratio of the gas. However, for the gases of interest in the flare stack environment, it has been discovered that gamma and molecular weight are not independent parameters but are related to each other. Thus, in some petrochemical refinery situations, molecular weight MW and gamma are found to be both related to the sound speed and hence to one another. To the extent therefore that MW and gamma are not independent variables, and to the extent their relationship is single valued, MW is calculable solely from C (and T). For simplicity of illustration, the empirical relationship of gamma to molecular weight, illustrated in FIG. 5, can be approximated by the equation:

$$\gamma = aMW + b \quad \text{(Equation 12)}$$

Then, using Equations 11 and 12, MW = (aMW+b)RT/$C^2$ from which MW = (bRT/$C^2$)/(1−aRT/$C^2$). Therefore, using an intervalometer to measure both speed of sound in the gas C and flow velocity V enables the instrument to determine the value of MW and then gamma.

INSTALLATION OF ACOUSTIC TRANSDUCERS BY HOT TAPPING

Referring to FIG. 2, a first step in installing the acoustic flowmeter is to properly position the sensing transducers 36 and 38 at precise locations on the pipe or conduit (i.e. header) through which the as will travel. Typically, the conduits are already in place and are closely positioned, adjacent to one another. Further, transducer installation should take place without interfering with the normal gas flow in the header. As a result, a hot tapping technique is employed using a new installation approach which is based upon aligning the structural and cutting elements from precisely located center positions on the conduit wall.

Figure 6:
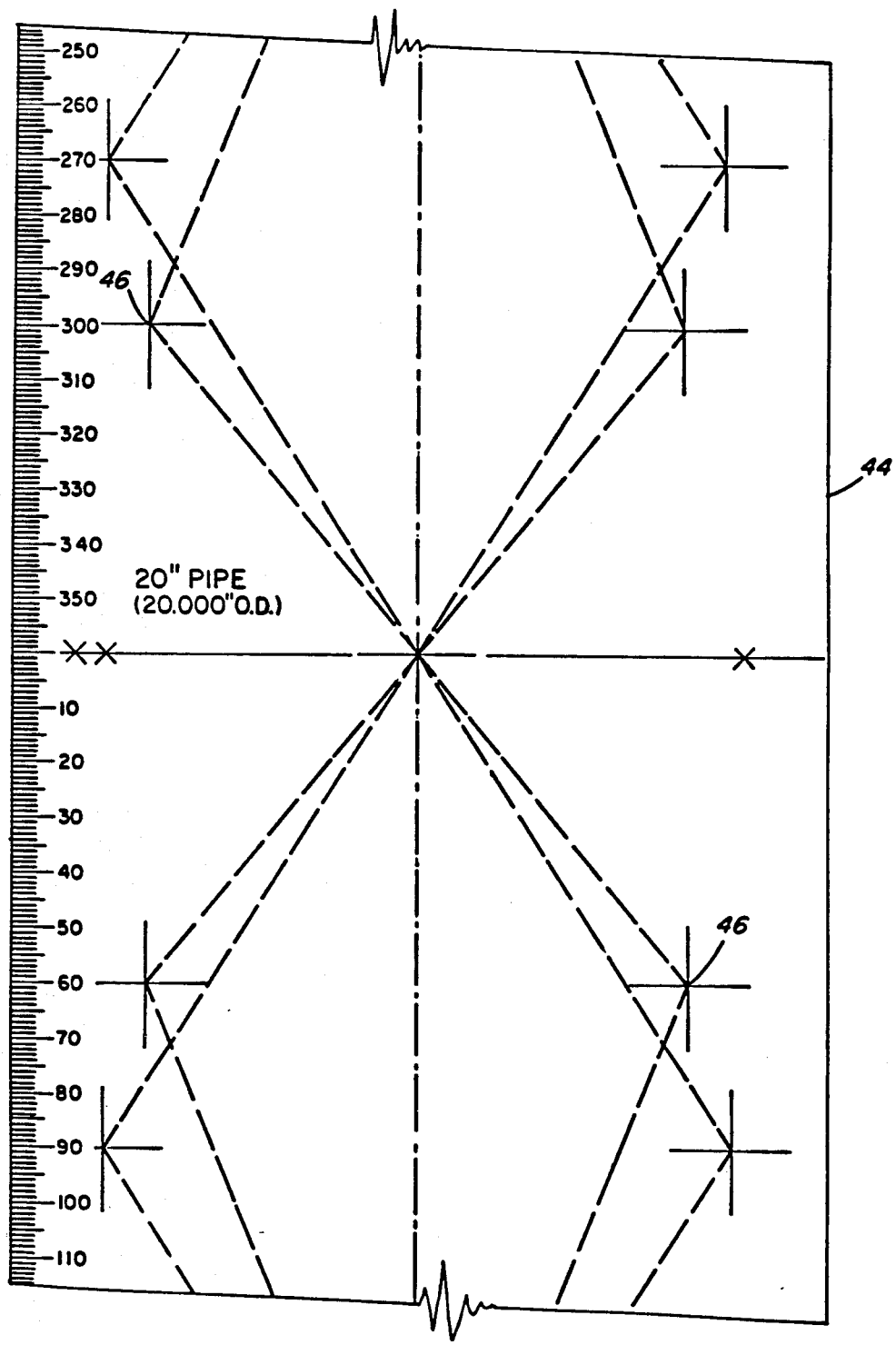
FIG. 6 is a graphical representation of an overlay template pattern according to a preferred embodiment of the invention.

In accordance with the present invention, a template 44 is prepared (for example, a mylar overlay), marked for the particular pipe size of interest (FIG. 6). The top of the pipe is located and the template is wrapped around the pipe using "match marks". A center location(s) 46 of the connection (to be used later) can then be marked with a centerpunch or by the intersection point of scribed lines. In an alternate embodiment, a blind location hole can be drilled perpendicular to the contoured conduit surface.

Preferably, in addition, vertical and horizontal scribe lines 48, 49 are marked on the pipe using the template. These scribed lines are employed to aid in locating a starter block or "boss" 50.

Figures 7, 7A:
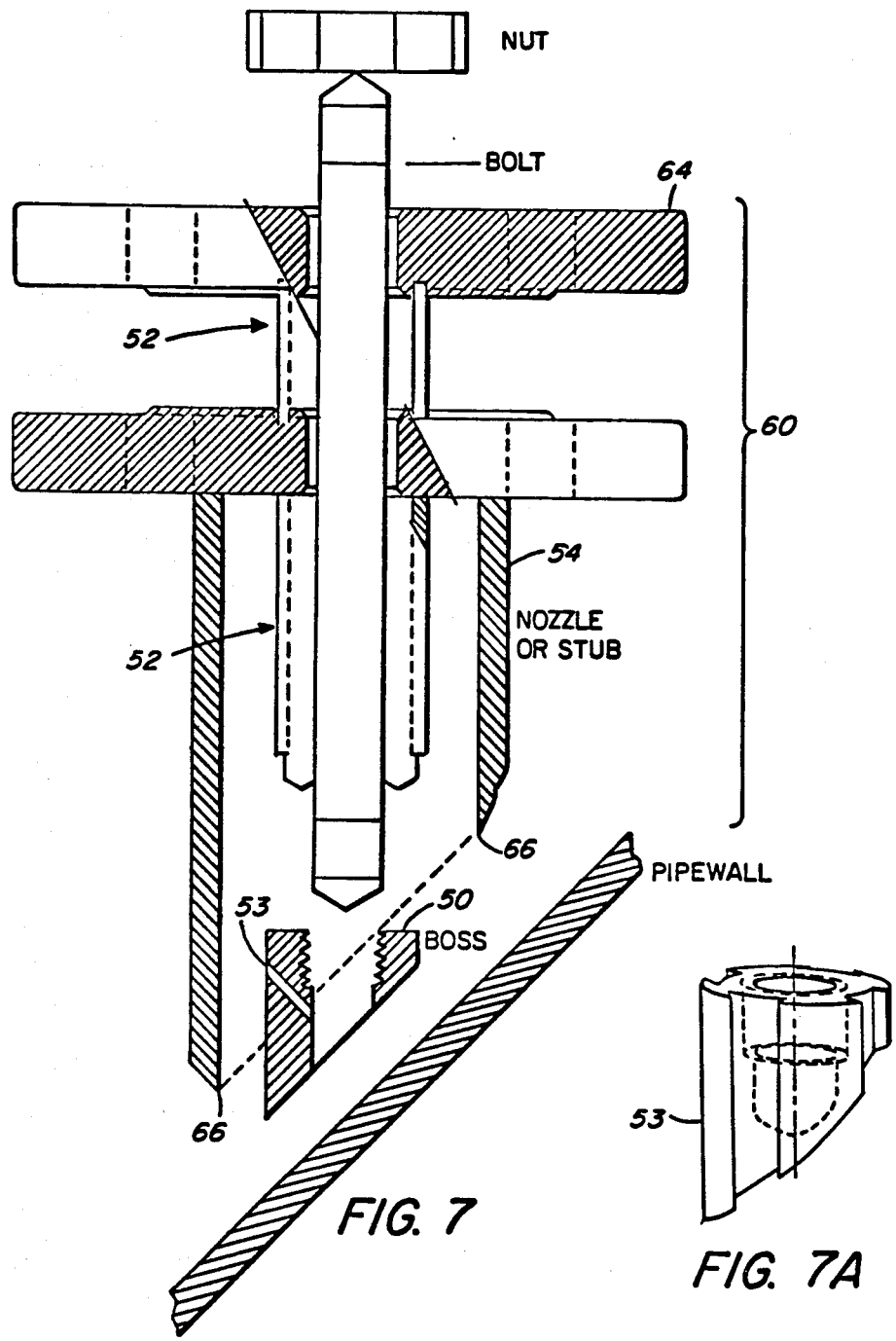
FIG. 7 is an assembly view of apparatus for accurate placement of the transducers in the conduit wall.
FIG. 7A is a more detailed view of the boss of FIG. 7.

Referring to FIGS. 7 and 7A, the boss 50 is employed for accurately positioning a jig 52 which will be used to hold a pipe stub 54 in place for welding. Bosses for each pipe size can be prepared for any of the various types of angular hot taps, that is, taps at 90°, 63°, or 45°. The bosses are first aligned to the pipe and clamped into position while they are tack welded to the pipe. Alignment can be performed following at least two approaches. In one approach, the boss is lined up with the pipe using the scribed lines transferred to the pipe from the mylar overlay. In a second approach according to the invention, the boss is contoured to mate with the conduit's exterior surface. Using either approach, a location hole 53, drilled through the boss perpendicular to the boss bottom contoured surface, typically at the center of the contoured surface, provides a reference mounting position for the boss. Thus, a pointed rod, such as a nail, slides through the location hole 53 and into the (centerpunched) indentation on the pipe. This location point, together with the contoured surface of the boss (following the second approach), uniquely positions the boss. In either case, the boss is then tack welded or otherwise firmly attached to the pipe.

Next a mating coupling 60 is positioned around the boss. This coupling is typically a welded assembly of the nozzle or "stub" 54 having welded thereto a blank slip-on flange 64 which has been bored to a press fit condition. A template is employed for cutting the stub end 66 to mate with the contour of the pipe wall. The stub ends are then beveled.

The jig 52 is next bolted to the stub 54 and together, the bolted and welded coupling assembly 60 is bolted to the boss. The boss is welded slowly to the pipe, at opposite sides as necessary, to maintain a proper orientation relative to the pipe. (In an alternate embodiment, the mating coupling, stub 54, can be directly positioned around the starter block, i.e. boss 50, in contact with the conduit, and connected by, for example, welding. A detailed description of this alternate embodiment is found in Warburton and Lynnworth, "Hot Tapped Ultrasonic Flowmeter Ports in Hot Steel Pipe", Advances in Test Measurement, Vol. 20, Instrument Society of America, May, 1983, which is incorporated herein by reference.) After welding, the jig is removed, the welds are tested, a valve is installed, and then the hot tap is made.

Hot tapping can be executed by installing a twist drill through a valve and packing gland in a hot tap machine and therefter penetrating the pipe. The twist drill is then withdrawn through the valve and packing gland and thereafter a long hole saw or cutter bit with a suitable device to catch the "coupon", is installed. A cut in the pipe wall is then made, the coupon withdrawn, and the tap is ready for installation of the sensors. The sensors are then intalled as is well known in the field, the interior threads of the coupling being sealed with teflon tape or another acceptable sealer. Thereafter, a second transducer is installed at a corresponding "opposite" location. This procedure can be carried out on a "live" pipe as well as on an empty one in a machine shop or field service depot. The advantage to the method becomes quite apparent for pipes which are very large compared to the available shop milling or boring machines.

ACOUSTIC TRANSDUCER INSTALLATION POSITIONING

Figure 8B:
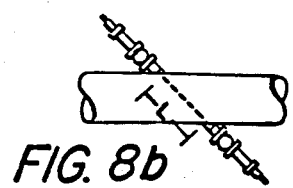
FIGS. 8a–8q show different placements of transducers in a conduit.
Figure 8C:
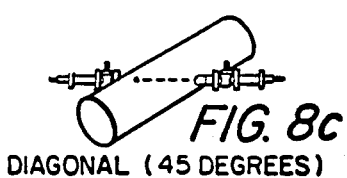
Figure 8D:
Figure 8E:
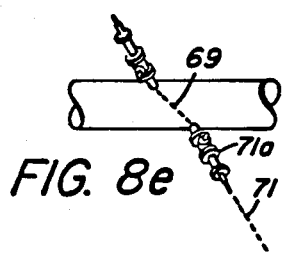
Figure 8F:
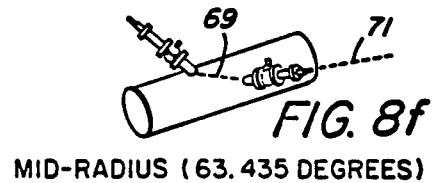
Figure 8G:
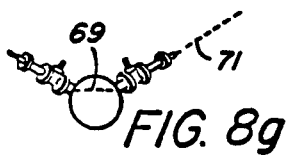
Figure 8H:
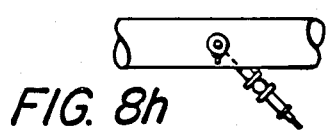
Figure 8I:
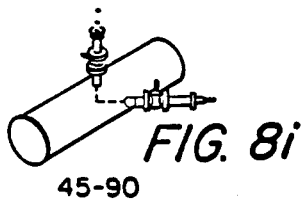
Figure 8J:
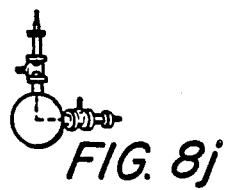
Figure 8K:
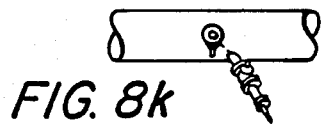
Figure 8L:
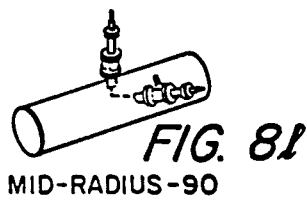
Figure 8M:
Figure 8N:
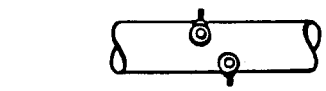
Figure 8P:
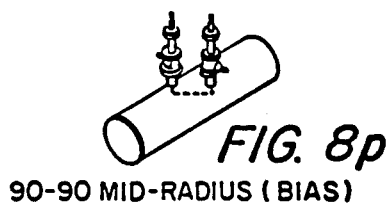
Figure 8Q:
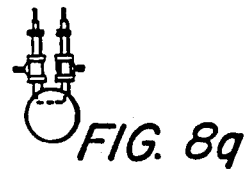
Figure 8A:
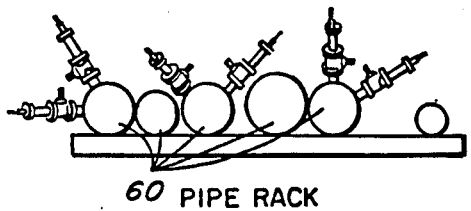

Referring now to FIGS. 8a–8q, the acoustic transducers or sensors are typically installed on conduits or pipes 60 preexisting in a manufacturing installation. The installation typically has a plurality of pipes, arranged in a closely spaced linear array (FIG. 8a), with little room for installation of the transducers.

The geometric relationship of the transducers is flexible. Several geometric configurations can be satisfactorily employed. Typical configurations can be characterized as (a) the mid-pipe 45° diagonal path (FIGS. 8b–8d), (b) the mid-radius 45° diagonal path (FIGS. 8e–8g), (c) the 45°–90° path at mid-pipe (FIGS. 8h–8j), (d) the 63°–90° path at midradius (FIGS. 8k–8m), and (e) a 90° bias path at 45° across the piper (FIGS. 8n–8q). The use of these various configurations will depend in part upon the particular geometry available to the installer. In addition, other variations can be employed depending upon the pipe geometry, for example, the path can be parallel to the pipe axis.

The first configuration, the conventional tilted diameter or mid-pipe 45° diagonal path, FIGS. 8b–8d, probably has the greatest usefulness. The transducers are at or near the pipe inside wall and provide a speed of sound measurement over a tilted diametric path having an axial component L.

The transducers, however, can also be placed in different locations with respect to the pipe diameter as dictated by the gas properties. Thus, for pipes so large that the acoustic path would be too long, or where access to the pipe is restricted so that the mid-pipe 45° diagonal path cannot be used, the sensors can be moved closer together such as one moved to the middle of the pipe (FIGS. 8h, 8i, 8j) or both moved inward toward the center. Thus a chordal segment can be used. Also, for small pipes, for which the acoustic paths would be too short for the "usual" placement at the lpipe inside wall, the sensors can be moved back into the pipe stubs or multiple reflections (FIG. 9) from within the pipe can be used. Recessing the transducers provides one method of flow-surveying pipes of different diameters while keeping the fluid path constant.

A second configuration having considerable practical potential for obtaining accuracy in both laminar and turbulent flows, where neighboring pipes restrict access, is the mid-radius path (FIGS. 8e, 8f, 8g). The transducers are installed in the pipe walls at or near the mid-radius location. In one combination, the pipe stubs are positioned at an angle of approximately 63° to the pipe, such that the angle beween the transducer axis (which is this illustrated embodiment is assumed to be coaxial with the interrogation path 69), and the axis 71 of the transducer holder tube 71a is 150°. In another configuration, the stub axis is normal to the pipe. This is an easier geometry for hot tapping. In either configuration, the sensors are pointed across the pipe at an angle, typically 45°. The acoustic measurements, in any configuration, are then obtained, as noted above, by "alternately" interrogating upstream and downstream.

Irrespective of which pipe installation configuration is employed, care must be taken to properly calibrate the measured readings with respect to what is often called the meter factor K. This factor relates the sampled flow to the area averaged flow of the fluids as they pass through the pipe with various flow profile distributions. For a turbulent flow, the flow velocity of fluid near the center axis of the pipe is greater than the flow velocity at or near the inside wall of the pipe. Thus, an axial path which extends at the center axis of the pipe, requires that the measured flow be reduced, that is, be multiplied by a factor less than one, while a similar axial measurement taken near the inside wall requires that the measured flow be increased, that is, be multiplied by a factor greater than one. For example, the meter factor K for the conventional mid-pipe 45° diagonal path is well known and, for turbulent flow, is:

$$K = 1/(1.119 - 0.011 \log Re)$$

where Re is the Reynolds number.

The meter factor K referred to above depends upon how the average velocity in the sampled path compares with the area averaged flow velocity. As an example, for a tilted chord segment (FIGS. 8n, 8p, 8q) the meter factor K depends on at least three factors: the distance from the axis to the plane containing the path, the projected path length which may be symmetrically distributed about a vertical center line and the Reynolds number. Other factors which influence the profile, and hence the meter factor, are pipe roughness, the transducers themselves, upstream conditions, etc.

For the tilted chordal segment path of FIGS. 8n, 8p, 8q, and for a smooth wall straight pipe having an inside diameter of 14.5 inches, the meter factor can be calculated under the following assumptions. If the path is in a horizontal mid-radius plane, symmetrical about the vertical center line, and has a projected path length of 12 inches in the end view, and if the profile disturbance due to the probes themselves can be neglected, then at a Reynolds number of $10^5$, the meter factor is 0.89. This value of K is some 11% lower than if the mid-radius chordal path extended all the way to the walls, for which latter path, as is well known, K is substantially unity for bot laminar and turbulent profiles.

Figure 9:
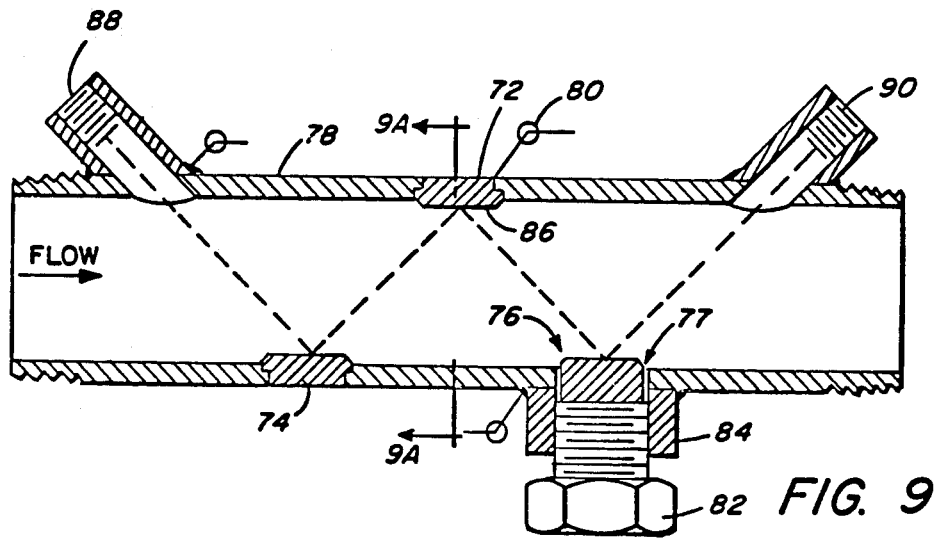
FIG. 9 schematically represents a multiple reflection path geometry in a restricted pipe configuration.

Referring now to FIG. 9, as noted above, the line of sight interrogation path through the fluid may not be long enough and therefore a reflection off the interior pipe wall may be needed to effectively lengthen that interrogation path. The same geometry can also be required when access to the pipe is limited to one side only, for example, a buried pipe. Referring to FIG. 9, special reflectors 72, 74, 76 are introduced within the "flow cell" either (a) to obtain a better reflection by virtue of reflectors made of materials such as stainless steel, Teflon(polytetrafluroethylene) or titanium which remain clean or are easily cleaned during maintenance procedures, or (b) to increase the effective axial projection of the interrogating beam over what the practical limit would have been in the absence of the reflector. In the illustrated embodiment, three reflectors are provided on the "folded" interrogation path although in other embodiments more or fewer reflectors can be employed. Reflector 72, which may be made of stainless steel, is installed from within the flow cell (for example through an opening 77) and is captured by the reverse counterbore of the pipe wall 78. The pipe is typically carbon steel, but in some applications may be made of fiberglass or other materials. The weld symbol 80 indicates a preferred method of securing reflector 72 to the wall for preventing leaks.

Figure 9A:
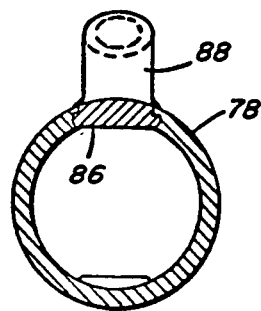
FIG. 9A is a cross-sectional view along lines 9A—9A of FIG. 9.

Reflector 74 can be similarly captured and secured or it may be held in place by epoxy and operate with a conventional O-ring (not shown) to maintain a seal. A third reflector, 76, is an extended portion of a pipe plug 82. The plug 82 is removably installed in a coupling 84 which can be welded to the pipe wall. An end view (FIG. 9A) shows that the reflectors protrude slightly into the flow stream. This projection is intentional and is designed to enhance the cleaning effect of the flowing fluid. In other instances, it may be desirable, or preferable, to have the reflectors flush with or even slightly recessed from the pipe interior wall.

In practice, a preferred upper limit on the diameter d, or largest principal dimension, of the flat reflecting face of the reflector (such as a face 86) is equal to twice the diameter of the transducer aperture created by the transducer ports 88 and 90.

In those instances where access to the conduit is available only from one side, and where a "V" path employing a reflector is too long for example because of attenuation in the fluid due to turbulence or absorption, an insertable probe 92, carrying both transducers 36 and 38, can be employed. Probe 92 is inserted into the conduit through a single opening. While insertable probes are well known in connection with turbine flow meters, pitot tubes, and momentum devices, etc., they are particularly advantageous in the ultrasonic flowmeter because they have no moving parts, are clog-free, have fast response, and high accuracy. A particularly difficult problem in connection with the ultrasonic insertable probe, however, in acoustic isolation of the transmitting element from the receiving element. Because strong support is required to withstand the fluid forces on the probe, as well as to avoid fatigue and failure due to vibration induced by vortex shedding, if only one small diameter port is made available for the device, there is not much distance between the transmitter and receiver. As a result, the illustrated ultrasonic insertable probe is constructed to achieve maximum acoustic isolation between the transducers and employs alternate materials of differing acoustic impedance to provide better acoustic isolation, gasket or sealant materials having high attenuation such as fibrous materials, minimum area of contact between parts which are to be isolated, and circuitous and preferably damped paths.

Referring to FIG. 10, the combination of these isolation principles provides an insertable flow meter structure wherein the transducers 36 and 38 are epoxied to a swage-type fitting 92, 94, respectively, which seal against cylindrical surfaces by employing metal or, for better isolation, Telfon (polytetrafluorethylene) ferrules. In some instances, a circuitous path 96 can be introduced around a rod or tube support 98. The ferrule seals against the path 96.

Dampening material 100 can be introduced in contact with as much of the structure as possible. The circuitous path 96 also provides a way of sealing a metal ferrule around a properly swaged thin tube where the structural element 98 inside the path 96 can be so thick-walled as to prevent standard tightening procedures from achieving the degree of swage deformation which is desired for a safe seal. The accurate determination of the area average flow velocity from interrogation over the acoustic paths 102 then involves the normal calibration, selection of appropriate meter factor, and precise knowledge of the interrogation path geometry.

ELECTRICAL FUNCTIONS

Again using the flare stack system for purposes of illustration, the electrical analysis and measurement apparatus 32 receives signal data from a plurality of flare stack headers and provides output information regarding the volumetric flow and the mass flow rate as a function of time for each header. The electrical apparatus, to provide an accurate measurement of both speed of sound in the fluid medium and the velocity of the fluid, when the parameters describing the fluid are changing rapidly (e.g. at a 10 Hz rate), measures rapidly and repeatedly the upstream and downstream transit times. Accordingly, in the illustrated embodiment, the acoustic interrogation using transducers 36 and 38 is made approximately eighty times per second, preferably alternating in a serial manner. The direction of interrogation thereby changes approximately eighty times per second, to provide an accurate measurement of the flow in spite of rapid pressure and media composition variations. In this example, the acoustic signal reversal is thus considerably faster than two times the rate of change of the highest significant frequency of either the sound speed or the fluid velocity. This provides a "sampling" rate which satisfies the Nyquist criterion. Other rapid interrogation patterns, designed to satisfy the Nyquist criterion could also be employed.

In the illustrated embodiment, "alternate" is used in connection with the invention to describe changing the direction of path interrogation from an upstream direction to a downstream direction. Importantly however, "alternating direction" is also intended to include changing directions after a finite (and usually small) number "n" of interrogations have been attempted or completed in a given direction. In fact, if the transducers are so well damped, that in the few milliseconds that it takes for a pulse to traverse a 0.3 to 1 meter path in a typical gas-filled conduit the excited transducer calms down enough to behave as a quiet receiving transducer, then "alterate" can include simultaneously energizing both transducers, and the received pulses will each have sampled essentially the same fluid portion in the conduit. (By calming down is meant to a level at least 20 dB below the level generated upon receipt of a fluid-borne acoustic pressure pulse.) Thus, in the extreme, alternating directions can include simultaneous excitation of an upstream-downstream transducer pair. As noted above, in any case, the net result is that the data collected provides a sampling rate which satisfies the Nyquist criterion.

It is also important to recognize that "pulse" as used herein includes a packet of ultrasonic energy, which can be coded or modulated in amplitude, phase, or frequency, and which can be said to repetitively but not continuously occupy a given space in the conduit during a given time interval. Thus in the extreme, the "pulse" can include a continuous wave signal which is periodically modulated and received using a matched filtering method.

The microprocessor controlled electrical apparatus 32 of the present invention is thus designed to measure, precisely, reliably, and quickly, the time interval between the transmission of a pulse from one transducer and its receipt generally but not necessarily at a different transducer. The illustrated electrical excitation signal is a time limited pulse 104, such as that illustrated in line (a) of FIG. 11. However, the transmitted acoustical pulse is relatively narrower in frequency due to transducer and transducer housing resonances and the received pulse, further influenced by attentuative filtering by the fluid, has the appearance of the pulse 106, illustrated in line (b) of FIG. 11. This pulse often has a relatively slowly increasing amplitude, that is, the difference in amplitude from "peak" to "peak" is relatively small either because of the inability to fabricate a suitable broadband transducer, because of intentional bandlimiting to reduce noise, because of filtering by the medium, or a combination of these reasons. (In other embodiments of the invention, other acoustic excitations could be employed, such as, for example, modulated continuous wave signals, a burst of a square wave signal, a sine wave modulated by a truncated guassian or cos n, where n is a positive integer, etc. In these other cases, the electrical circuitry would necessarily be different to accomodate the different excitation signals.)

For the pulse shown in FIG. 11 at line (b), a pulse having a "Q" of about ten, the difference in amplitude from amplitude peak to amplitude peak near the beginning of the pulse may be only ten percent, i.e., about one dB. Consequently, small amounts of noise or other interference can easily upset an amplitude threshold arming procedure, after which arming, the first zero crossing determines the time of arrival of the pulse signal. As noted above, the shape of the pulse in line (b) of FIG. 11 occurs in principal part due to resonant effects of the structure of, for example, the pipe walls, the layered media through which the pulse is traveling, or natural resonances in the transducers used for the ultrasonic pulse transmission and reception. Material characteristic resonances can also affect the received signal pulse shape.

Accordingly therefore, the usual arming methods which are based solely on the amplitude of the received signal are not sufficiently reliable for the narrow band signal. As noted above, the change of amplitude from one cycle to the next, for a signal having a "Q" of about ten, is not in excess of about ten percent or one dB. Therefore, if jitter in the received signal exceeds one dB, the zero crossing detector will often be falsely armed at the wrong cycle if the conventional amplitude-based arming method is used.

Figure 12:
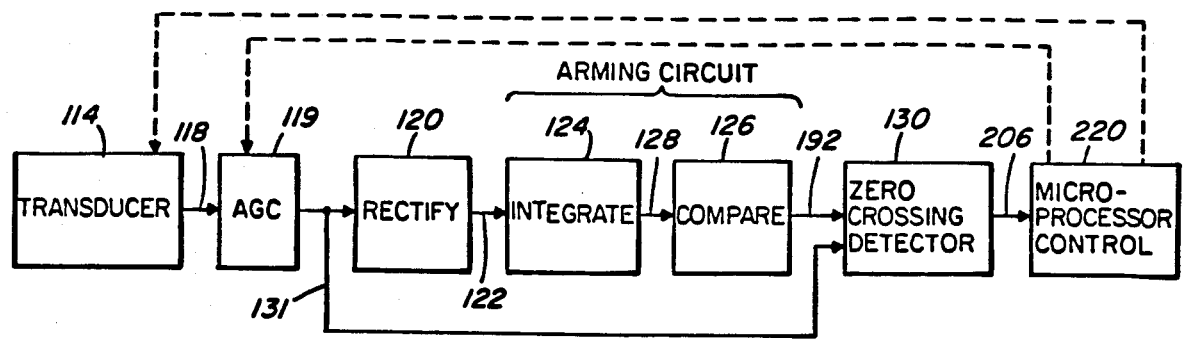
FIG. 12 is an electrical block schematic showing the major components according to the invention.

According to the invention therefore a different arming method and apparatus are employed. Referring to FIG. 12, in the illustrated embodiment of the invention, a transducer 114 provides a received output signal over a line 118. The transducer 114 is representative of the plurality of transducers mounted in the headers. Electrical circuitry corresponding to that described below would be employed (or the same circuitry is switchably connected) in connection with each such transducer. The received signal, in the illustrated embodiment, is processed through an automatic gain control circuit 119 and is half-wave (or full-wave in other embodiments of the invention) rectified by a rectification circuit 120. The rectified output over a line 122 is then integrated by an integration circuit 124. A comparison circuit 126 compares output 128 of the integrator, for each pulse, to a preset threshold value. When the output of the integration crosses the threshold value, the apparatus is then armed and an event detector 130, here shown as a zero crossing detector, detects the next event (the next zero crossing) in the input received signal over a line 131. Rectification may be either full wave of half wave; however, according to the preferred embodiment of the invention, half wave rectification is preferred. The particular arming method and apparatus employed herein is particularly reliable and is substantially insensitive to noise and jitter as described hereinafter.

According to the integrated threshold arming method and apparatus, and referring to FIG. 11, line (c), the result of rectifying the received signal is a plurality of half-cycle sine waves 134 (approximately) at first increasing an amplitude and then decreasing in amplitude. According to the preferred embodiment, it is the cumulative sum of the areas under, for example, each (positive) half cycle of the received signal which is employed to mark (the arming condition) a zero crossing (or other event) which, in turn, is used to determine the actual arrival time of the energy pulse.

Figure 13:
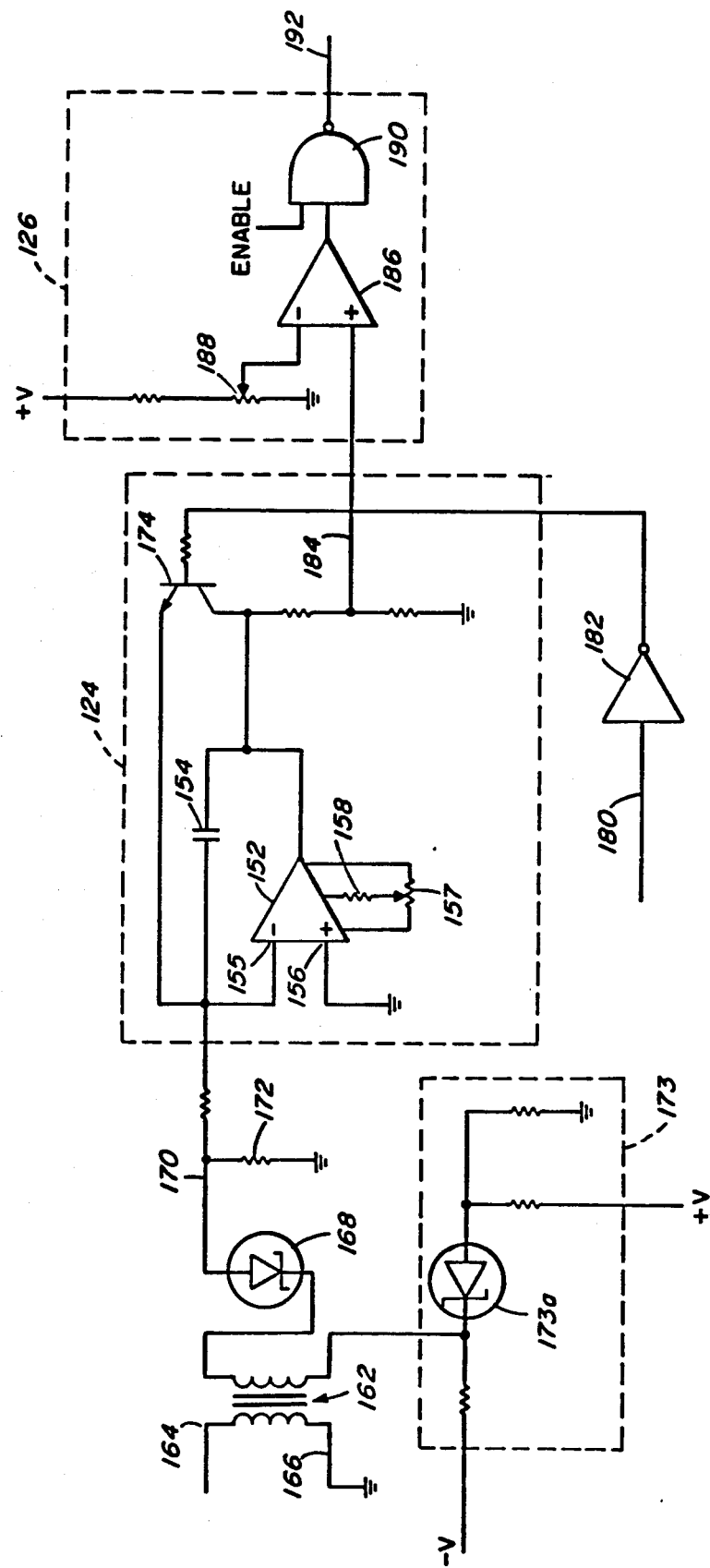

Referring now to FIG. 13, in a particularly preferred embodiment of the invention, the integration circuit 124 employs an operational amplifier 152 connected with a capacitor 154 in its feedback circuit connection to a negative amplifier input 155. The positive input 156 to amplifier 152 is grounded. An offset adjustment employing a potentiometer 157 and a series resistor 158 provides "zeroing" for the amplifier 152.

The input signal to the negative terminal input 155 of operational amplifier 152 is available from the rectification circuit 120. Circuit 120 has a transformer 162 which receives its input across input terminals 164, 166 (terminal 166 being grounded) and provides a rectified output (half wave rectification), from a rectifier 168, over a line 170. A resistor provides a load for a bias network 173 when the amplifier 152 is not in its linear region of operation. Bias network 173 has a rectifying diode 173a which provides temperature compensation for diode 168. Both diodes 168 and 173a are Schottky diodes.

In accordance with the invention, integrator 124 integrates the half cycles of a received pulse signal. To reduce noise problems and to "zero" the output of the integrator at the beginning of a received pulse, the integrator is in a "reset" state until just prior to the expected receipt of the input signal pulse. The reset function is enabled using a transistor 174 having its emitter and collector connected across the capacitor 154. At turn on (i.e. reset), the output of the integrator "ramps down" to about −0.1 volts. This takes approximately 0.1 to 0.2 milliseconds, the time being set by potentiomenter 157. The state of transistor 174 is controlled by the signal on its base which, at transistor turn-off, corresponds to a receive window during which a pulse of energy is expected to be available. At transistor 174 turn-off, the integrator 124 integrates the rectified signal on line 170.

Noise immunity is further enhanced by imposition of a deadband, that is, a voltage threshold below which the input signal is not integrated. In the illustrated embodiment, the deadband is provided by the turn-on voltage required for diode 168, typically about 0.4–0.5 volts for a Schottky diode. This voltage is effectively reduced further by bias network 173.

A receive gating signal is available over a line 180. The gating signal is inverted by an inverter 182 and is provided thereby to the transistor 174. The output of the integrator 124 available from a resistor divider, over a line 184, connects to the comparator 126. Comparator 126 employs a comparator integrated circuit 186, having one input connected to the integrator output over line 184 and its other input connected to the output of a potentiometer 188. Potentiometer 188 is connected between a reference voltage and ground. The comparator output is the arming signal and passes through a gating structure 190 and appears over a line 192. This signal changes state when the integrated signal from integrator circuitry 124 crosses the threshold value determined by potentiometer 188.

Figure 14:
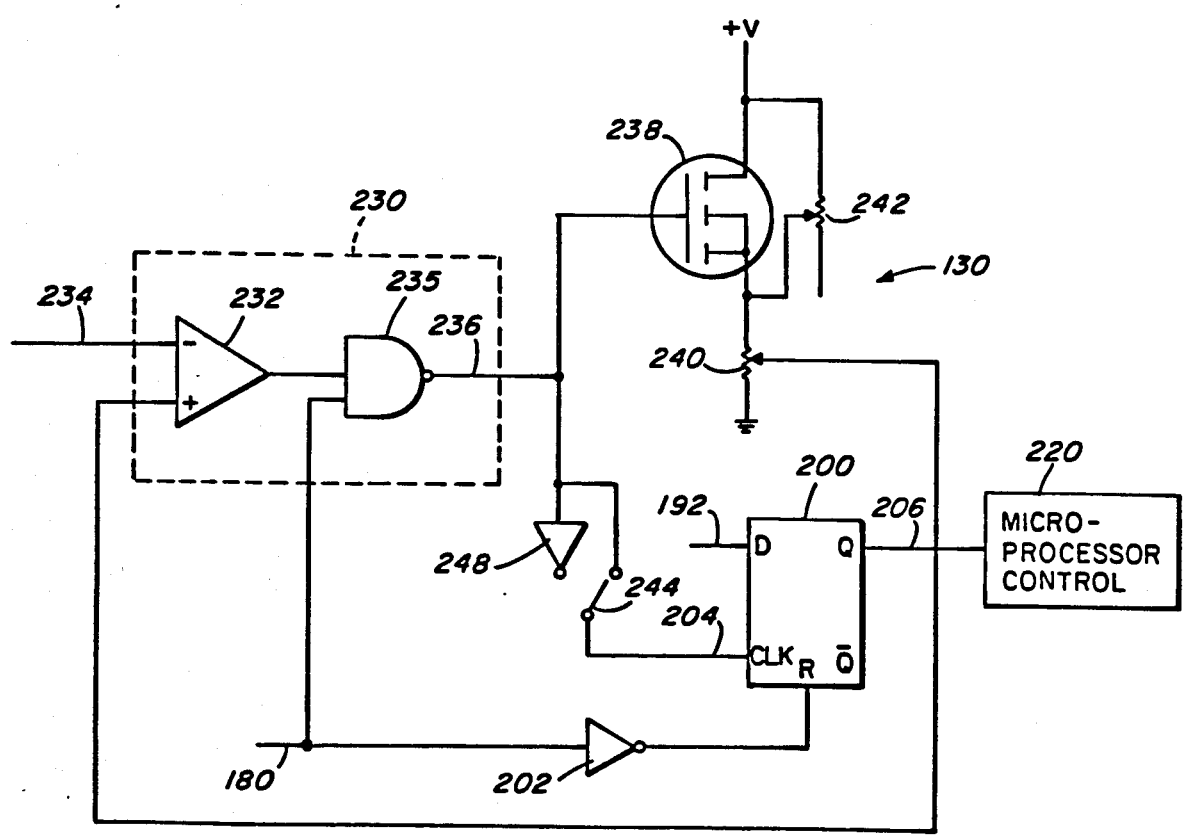
FIGS. 13 and 14 are more detailed electrical schematic diagrams describing a particularly advantageous implementation of the electrical circuitry according to the invention.

Referring to FIG. 14, the output of the integrated threshold circuitry over line 192, the arming signal, indicates an arming condition when the integrated value crosses the threshold value thereby changing the state of the output signal. This "change of state" enables an event recognition circuit, here the zero-crossing detector 130. Detector 130 employs a flipflop 200 which, when initially enabled, is in the reset state. Flip-flop 200 has been previously reset by the gating window signal over line 180 (through an inverter 202). When clocked by a signal over a line 204, the flip-flop 200 indicates a zero crossing in the transducer generated receive signal, and that zero crossing signal output of flip-flop 200 over a line 206, is provided to further circuitry including a microprocessor controller 220 to set the time of arrival of the received pulse.

The zero crossing detector 130 further employs a gated comparator 230 having a comparator integrated circuit 232, one side of which receives the electrical pulse receive signal from the transducer over a line 234. A gate 235 is enabled by the gating signal over line 180. The pulse signal over line 234 has been passed through an automatic gain control (AGC) circuitry to provide a substantially constant input signal amplitude level even though changes in the physical media being monitored may occur.

The zero crossing detector employs a varying threshold level to improve zero crossing detection precision. In operation, with no signal present, the output of the zero crossing comparator 230, over a line 236, maintains a MOSFET 238 in an "on" condition. The threshold level is thereby set by an arming level potentiometer 240. In the illustrated embodiment, this quiescent level is a non-zero positive voltage. Thereafter, when a signal pulse is received, comparator 230 changes the state of its output signal when the quiescent threshold is exceeded. This causes the MOSFET 238 to turn off, thereby placing a variable resistor 242 in series with potentiometer 240. The threshold level is thereby effectively lowered, variable resistor 242 having a resistance substantially greater than the resistance of potentiometer 240. Thus, as the input signal approaches zero, going from a positive to a negative voltage (for the position of a switch 244 illustrated in the drawing), the lower threshold crossing is marked by the change of state of the signal on line 236. It is this change of state which acts to clock the flip-flop 200 thereby marking, by a signal over line 206, the first negative going zero crossing occurring after the arming signal over line 192 is received. (In its other position, the switch 244 places an inverter 248 in series with the output of comparator 230 thereby causing detection of a negative to positive zero-crossing at the threshold level set by potentiometer 140.)

While the invention has been described with reference to a zero-crossing detector, it will be understood that the actual point to which time is measured at or after arming, can be any of a variety of signal threshold levels. For example, the level at which the arrival time is said to occur can be at any convenient absolute signal level, a selected fraction of the peak signal level, or even at a value greater than a particular cycle's maximum value, for example, at a level fifty percent greater than the peak value of the first cycle following arming. This last alternative can be selected for measuring time at a point where the signal-to-noise ratio is large enough to permit a particularly high accuracy to be obtained.

In this manner, the integrated threshold arming technique accurately, reliably, and repeatedly arms the event recognition detector at the same cycle of each received signal pulse over line 118.

In those embodiments where the transducers, the medium, and/or the interrogation structures allow a broadband acoustic pulse to be received, a more conventional arming method, for example a fixed amplitude threshold or a fixed percent of the peak amplitude, etc, can be employed.

AUTOMATIC GAIN CONTROL

Figure 15:
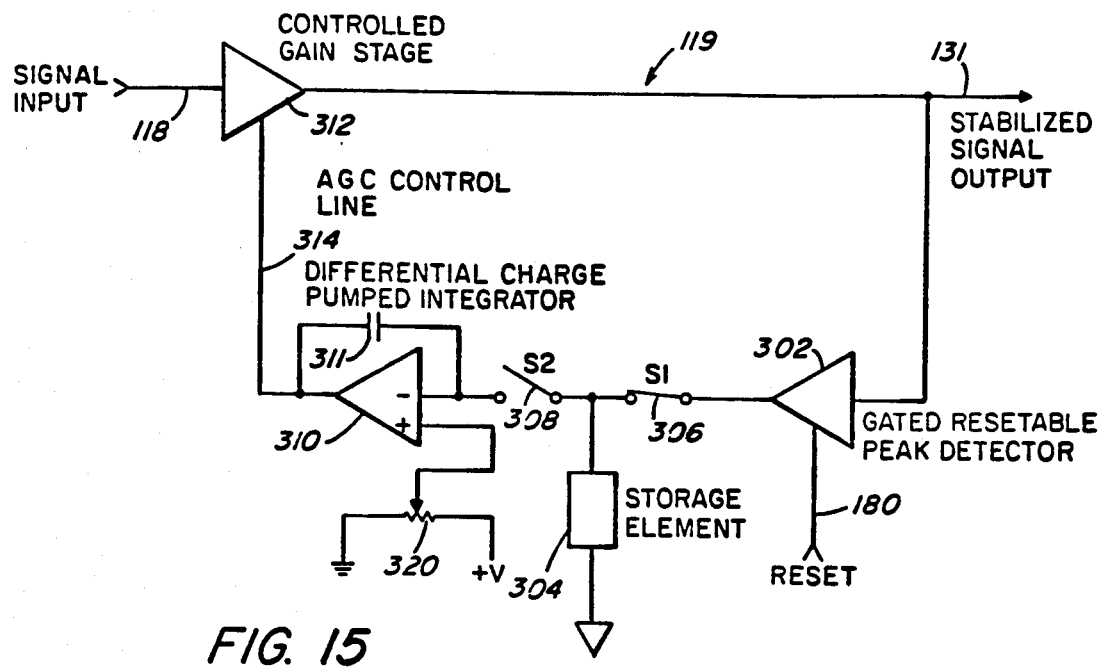
FIG. 15 is a schematic diagram of an automatic gain control circuit according to the invention.

According to the illustrated embodiment, the automatic gain control circuitry 119 is capable of tracking the envelope of signals with both rapidly increasing and rapidly decreasing signal amplitudes. Referring to FIG. 15, illustrated circuitry 119 has a gated, resettable, peak detector 302, a storage element 304, the storage element typically being a capacitor, switches 306 and 308, a differential "charged pumped" integrator 310, having an integrating capacitor 311 in its feedback loop, and a controlled gain amplifier 312, the gain being controlled by the automatic gain control signal level over a line 314. The input to the gain controlled amplifier is the "raw" input signal from, for example, the transducer 114 receiving the ultrasonic pulse energy in the fluid. The output of the transducer is provided to the gain control circuit 119 over line 118. The output of the gain controlled amplifier, over line 131, is thus a stabilized signal output which is delivered, inter alia, to the rectification circuitry 120 and the zero crossing detector 130. That stabilized signal output is also provided to the gated resettable peak detector 302 wherein the automatic gain control amplifier operates in a feedback loop configuration.

Figure 16:
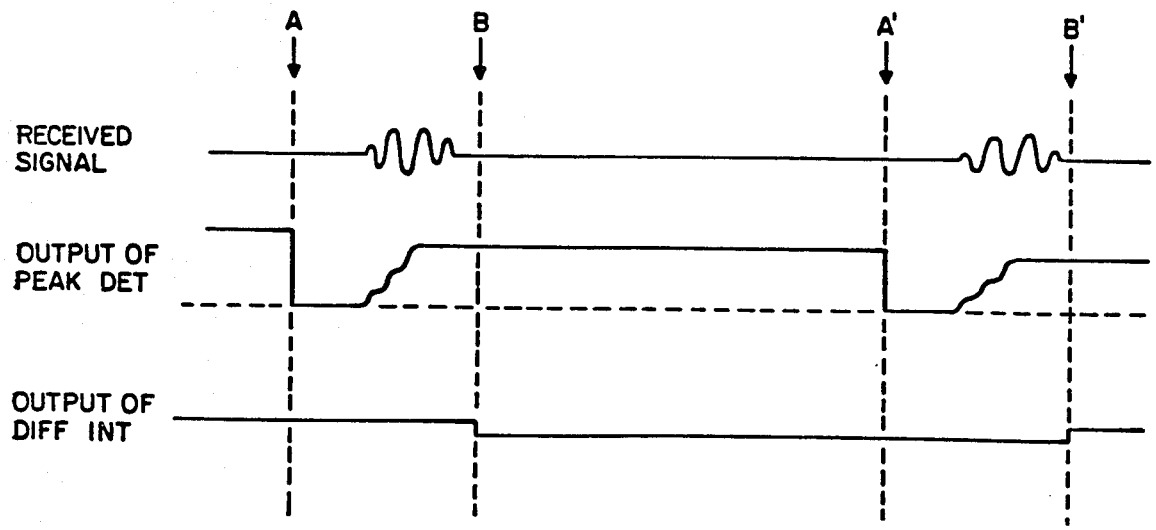
FIG. 16 is an illustration of the operation of the automatic gain control circuit of FIG. 15.

In operation, referring to FIGS. 15 and 16, at the beginning of a pulse, at time "A", the peak detector 302 has been reset to zero. The peak detector can be reset to zero using for example the receiver window pulse over line 180 (FIGS. 13 and 14). Upon receipt of the desired signal, the peak detector charges the storage element 304 to a voltage corresponding to the peak of the received signal. During this time, switch 306 has been closed and switch 308 has been open. After the pulse of energy has been received, switch 306 is opened and switch 308 is thereafter closed. This occurs at a time "B" after receipt of the energy pulse but before receipt of the next signal energy pulse.

When switch 308 is closed, some of the charge stored in the storage element 304 is "dumped" into the differential integrator 310. The quantity of charge injected into the integrator 310 is proportional to the difference between the signal amplitude control voltage determined by a potentiometer 320 and the actual received peak signal amplitude. The "dumped" charge causes the output of the integrator 310, which is the automatic gain control signal voltage, to apply a correcting voltage to control the gain of amplifier 312. The peak detector is thereafter reset by the gating signal over line 180, switches 306 and 308 reversing their condition, so that the storage element is discharged and the cycle repeats again for the next received pulse.

Figure 17:
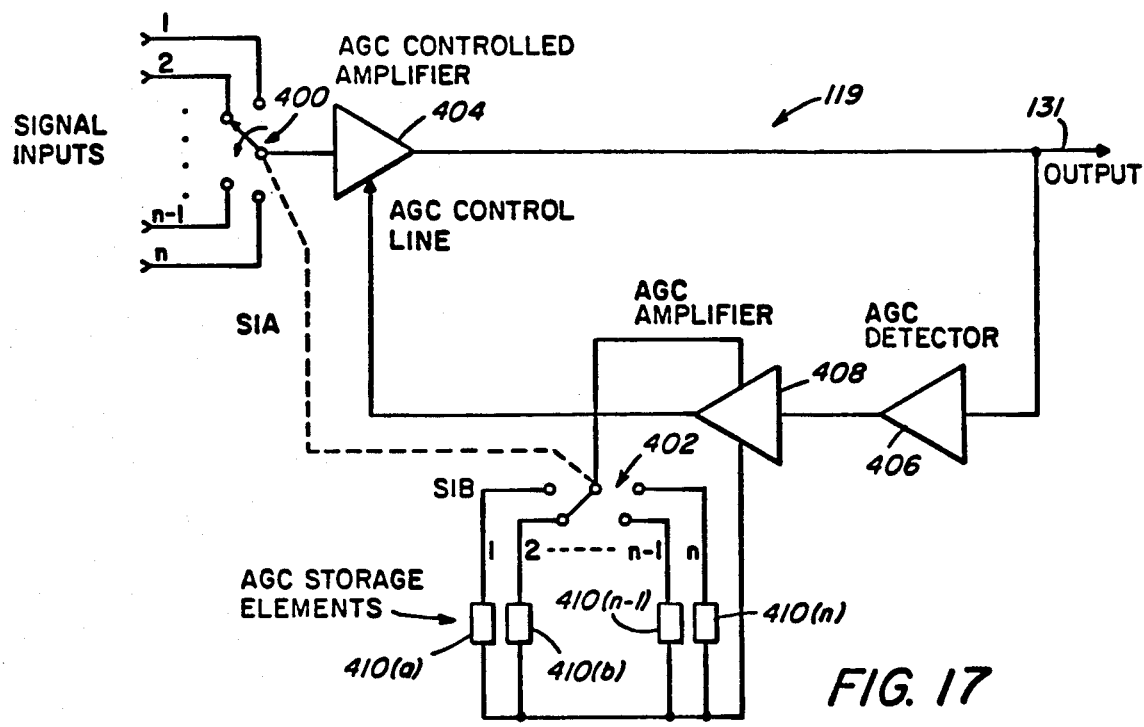
FIG. 17 is a schematic block diagram of a multipath automatic gain control circuit according to the invention.

Referring now to FIG. 17, according to the invention, a single automatic gain controlled amplifier receiver circuitry can be employed in connection with multiple measurement paths, corresponding to measurements in a plurality of headers, by employing a synchronized switching arrangement along with storage elements in association with each path. In accordance with this aspect of the invention, the circuitry includes multi-position switches 400, 402, which synchronously connect automatic gain controlled amplifier 404 and an automatic gain control peak detector 406, which operates in connection with an amplifier 408, to different paths (1, 2, ..., n−1, n) and different storage elements 410a, 410b, ..., 410n−1, 410n. Thus, according to the invention, each storage element is employed to hold accurate automatic gain control level data for an associated transmission path. By using a previously stored automatic gain control level for each path, the automatic gain control circuitry is capable of providing correct composition for each path immediately upon selection of that path.

Thus, switches 400 and 402 operate synchronously so that movement of switch 400 to a path "m", is automatically accompanied by the movement of switch 402 to connect storage element 410(m) to the circuit. The storage elements can also be updated each time a path is selected thereby allowing the automatic gain control loop to compensate for changes in the path dependent signal strength.

In addition, wherein multiple paths are measured using a single automatic gain control receiver, the automatic gain control circuitry described in connection with FIG. 15 is preferably employed. The FIG. 15 circuitry can be modified to allow use of multiple storage elements such as those shown in FIG. 17. The resulting AGC circuitry, illustrated in FIG. 18, operates in a manner identical to that described in connection with FIG. 15 except that synchronous switches 306, 308, are employed for providing the necessary switching circuity to synchronously hold and store the AGC control signals in capacitors 311(a), 311(b), ..., 311(n), and connect amplifier 312 to the correct input line.

Referring to FIG. 12, the microprocessor controller 220 operates to repetitively and alternately cycle the transducers 36 and 38 for interrogating the headers for determining, as a function of time, fluid velocity and speed of sound. The microprocessor control also operates and synchronizes the automatic gain control circuitry in accordance with the particular path being interrogated. Correspondingly therefore, the microprocessor receives data from the zero crossing detector and synchronizes that data with the particular path being interrogated.

Figure 18:
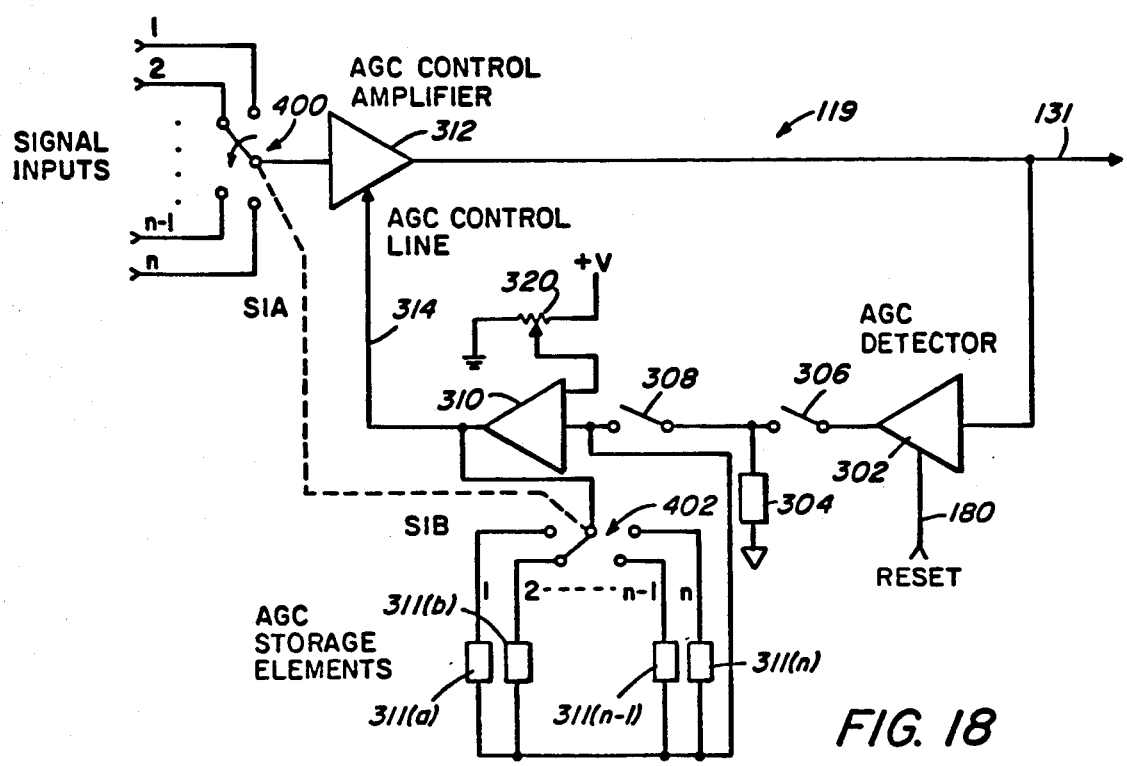
FIG. 18 is an electric schematic showing the automatic gain control amplifier of FIG. 15 in a multipath environment.

The microprocessor herein is also adapted, using the AGC circuitry of FIG. 18, to reliably and quickly switch between the various transducer pairs of the headers and to provide an output over time which reflects the flow rate and mass flow in the header. The multi-path AGC of FIG. 18 thus enables rapid switching even though the signal attenuation, in the different paths, or in opposite directions along the same interrogation path, can vary. Further, however, in order to avoid erroneous output readings, averaging is employed with a memory fading technique. This can be viewed as a form of boxcar averaging where, through weighing, data contributions of old "boxcars" are not as influential as the more recent data. This means that averaging is adjustably reponsive to transients. A typical weighting procedure, a truncated binary weighting method, is illustrated in the table below:

| Boxcar No. | Weight |
| --- | --- |
| 1 | 8 |
| 2 | 4 |
| 3 | 2 |
| 4 | 1 |
| greater than 4 | 0 |

Note that to obtain a smoother output, less responsive to transients, a more "elephant-like" memory, that is one that includes contribution from measurements made much earlier, can be employed. The resulting flow measurement apparatus thus quickly switches between several paths, quickly adjusts to each path using the multi-path automatic gain control amplifier circuitry, and accurately determines the arrival time of the incoming pulse in order to accurately provide the measures of absolute transit time (to determine the speed of the energy pulse in the fluid, and hence mass flow rate) and the time difference between upstream and downstream transit time to determine the volumetric flow rate.

The microprocessor control can also be employed to measure the temperature of the fluid without actually using an additional temperature sensor. If the design of the pulse generator by which the transducers are excited allows the center frequency of the transmitted pulse to be controlled by the resonant frequency of the transducer, or by a principal structural element of the transducer assembly, and if the resonant frequency is a known function of temperature, then the center frequency of the pulse can be employed as a measure of the fluid temperature. Therefore, the determination of mass flow rate, as discussed above in connection with Equations 2–11, can be accomplished without the need of an additional temperature transducer. In this instance, the microprocessor would have as an additional input a signal representing the resonant frequency of the received pulse. Circuitry for accomplishing this is well known in the art.

Similarly it is well known that the received acoustic signal level can be related, for calm flows, to pressure in the fluid. Therefore the microprocessor can determine a value of fluid pressure and temperature from the acoustic measurements. Thus mass flow rate, according to Equation 9, can be determined using solely the acoustic transducers.

Additions, subtractions, deletions, and other modifications of the described embodiment will be obvious to those practiced in the art and are within the scope of the following claims.

What is claimed is:

1. Apparatus for detecting a leak in a flare stack system, said flare stack comprising
    a plurality of processing stations,
    each processing station having associated therewith a safety discharge conduit and a safety discharge valve connected for controlling discharge from said processing station to said conduit,
    said apparatus comprising
    a header conduit connected to a plurality of different discharge conduits, and
    means for monitoring said header conduit for detecting said leaks, said monitoring means determining fluid flow velocity proximate said discharge conduits as a function of time, said monitoring means comprising
    first transducers at first locations in said header conduit proximate said discharge conduits,
    second transducers at second locations in said header conduit proximate said discharge conduits, corresponding ones of said first and second transducers defining between them an interrogation path proximate said discharge conduits,
    means for exciting said first and second transducers to emit acoustic energy,
    means for measuring an upstream transit time and a downstream transit time for the propagation of said energy between said transducers in an upstream and downstream direction respectively,
    means for controlling said excitation and measuring means for generating said transmit time measurements at a rate greater than at least ten times per second, and
    means for determining from said transmit times the speed of sound in said fluid proximate said discharge conduits as a function of time and the fluid flow velocity proximate said discharge conduits as a function of time,
    whereby a gas leak through said safety valves can be detected.

2. Apparatus for detecting a leak in a flare stack system, said flare stack comprising
    a plurality of processing stations,
    each processing station having associated therewith a safety discharge conduit and a safety discharge valve connected for controlling discharge from said processing station to said conduit, and
    a header conduit connected to a plurality of said discharge conduits,
    said apparatus comprising
    a first transducer at a second location in said header conduit, said first and second transducers defining between them an interrogation path,
    means for exciting said first and second transducers to emit acoustic energy,
    means for measuring an upstream transit time and a downstream transit time for the propagation of said energy between said transducers in an upstream and a downstream direction respectively,
    means for controlling said excitation and measuring means for generating said transit time measurements at a rate greater than at least ten times per second,
    means for determining from said transit times the speed of sound in said fluid as a function of time and the fluid flow velocity as a function of time, whereby a gas leak through said safety valves can be detected, and
    means for determining from said speed of sound in said fluid an average molecular weight of said fluid as a function of time,
    whereby an identification of the process station at which the leak occurred can be made.

3. The leak detection apparatus of claim 2 wherein said repeating means comprises means for repeating said measurements at a frequency greater than two times the highest frequency of significance of an expected average molecular weight as a function of time and an expected fluid velocity as a function of time.

4. Apparatus for detecting a leak in a flare stack system, said flare stack comprising
    a plurality of processing stations,
    each processing station having associated therewith a safety discharge conduit and a safety discharge valve connected for controlling discharge from said processing station to said conduit,
    said apparatus comprising
    a plurality of header conduits, each header conduit connected to a plurality of different discharge conduits, and
    means for monitoring each said header conduit for detecting said leaks, said monitoring means determining fluid flow velocity and average molecular weight for each header as a function of time, said monitoring means comprising
    first transducers at a first location in each header conduit,
    second transducers at a second location in each header conduit, corresponding ones of said first and second transducers defining between them an interrogation path,
    means for exciting said first and second transducers to emit acoustic energy, means for measuring an upstream transit time and a downstream transit time for the propagation of said energy between corresponding ones of said first and second transducers in an upstream and a downstream direction respectively, means for controlling said excitation and measuring means for generating said transit time measurements at a rate greater than at least ten times per second, and means for determining from said transit times the speed of sound in said fluid as a function of time and the fluid flow velocity as a function of time, whereby a gas leak through said safety valves can be detected.

5. A method for detecting a leak in a flare stack system, the flare stack system comprising a plurality of processing stations, each processing station having associated therewith a safety discharge conduit and a safety discharge valve connected for controlling discharges from said processing station to said conduit, said method comprising the steps of connecting a header conduit to a plurality of discharge conduits, monitoring said header conduit for detecting said leaks, and determining fluid flow velocity proximate said discharge conduits as a function of time, said monitoring step comprising the steps of exciting first transducers and second transducers for emitting acoustic energy, said first transducers being positioned at a first location in said header conduit proximate said discharge conduits and said second transducers being positioned at a second location at said header conduit proximate said discharge conduits, measing an upstream and a downstream transit time for propagation of said energy between said transducers in an upstream and a downstream direction respectively, repeating said excitation and measuring steps at a rate greater than at least ten times per second, and determining from the transit times, the speed of sound in said fluid proximate said discharge conduits as a function of time and the fluid flow velocity proximate said discharge conduits as a function of time, whereby a gas leak through said safety valves into the flare system and to the flare stack can be detected.

6. The leak detection method of claim 5 further comprising the steps of connecting a plurality of header conduits, each header conduit being connected to a plurality of different discharge conduits to a main flare stack header, monitoring said main flare stack header for detecting a said leak therein, and determining fluid flow velocity and average molecular weight for said main flare stack header as a function of time.

7. A method for detecting a leak in a flare stack system, the flare stack system comprising a plurality of processing stations, each processing station having associated therewith a safety discharge conduit and a safety discharge valve connected for controlling discharges from said processing station to said conduit, and a header conduit connected to a plurality of said discharge conduits, said method comprising the steps of exciting a first transducer and a second transducer for emitting acoustic energy, said first transducer being positioned at a first location in said header conduit and said second transducer being positioned at a second location in said header conduit, measuring an upstream and a downstream transit time for propagation of said energy between said transducers in an upstream and a downstream respectively, repeating said excitation and measuring steps at a rate greater than at least ten times per second, determining from the transit times, the speed of sound in said fluid as a function of time and the fluid flow velocity as a function of time, whereby a gas leak through said safety valves into the flare system and to the flare stack can be detected, and determining from said speed of sound in said fluid an average molecular weight of said fluid as a function of time, whereby an identification of the process station at which the leak occurred can be made from said determined average molecular weight of said fluid.

8. The leak detection method of claim 7 wherein said repeating step comprises the step of repeating said measurements at a frequency greater than two times the highest frequency of significance of an expected average molecular weight as a function of time and an expected fluid velocity as a function of time.

9. A method for detecting a leak in a flare stack system, said flare stack system comprising a plurality of processing stations, each processing station having associated therewith a safety discharge conduit and a safety discharge valve connected for controlling discharge from said processing station to said conduit, said method comprising the steps of connecting a plurality of header conduits, each header conduit being connected to a plurality of different discharge conduits to a main stack header, monitoring each said header conduit for detecting a leak therein, and determining fluid flow velocity and average molecular weight for each header as a function of time, said monitoring step including the steps of exciting first transducers and second transducers for emitting acoustic energy, said first transducers being positioned at a first location in each header conduit and said second transducers being positioned at a second location in each header conduit, measuring an upstream and a downstream transit time for propagation of said energy between corresponding ones of said first and second transducers in an upstream and a downstream direction respectively, repeating said excitation and measuring steps at a rate greater than at least ten times per second, and determining from the transit times the speed of sound in said fluid as a function of time and the fluid flow velocity as a function of time, whereby a gas leak through said safety valves into the flare system and to the flare stack can be detected.

* * * * *

UNITED STATES PATENT AND TRADEMARK OFFICE
CERTIFICATE OF CORRECTION

PATENT NO. : 4,856,321

DATED : August 15, 1989

INVENTOR(S) : Jack W. Smalling, Leonard D. Braswell and Lawrence C. Lynnworth Page 1 of 2

It is certified that error appears in the above-identified patent and that said Letters Patent is hereby corrected as shown below:

Column 1, line 54 delete "slose" and insert --close--.

Column 8, line 15 delete "tansit" and insert --transit--.

Column 9, lines 16 and 17, delete
"$C_C = C_O - [(2.11 \times 10^{-8})C_O^2 + (7.5 \times 10^{-4}) C_O](-T_O-100)$ (Equation 6)"
and insert
--$C_C = C_O - [(2.11 \times 10^{-8})C_O^2 + (7.5 \times 10^{-4}) C_O](T_O-100)$ (Equation 6)--.

Column 10, line 35 delete "as" and insert --gas--.

Column 17, line 9 after "resistor" insert --172--.

Column 21, line 63 delete "transmit" and insert --transit--.

UNITED STATES PATENT AND TRADEMARK OFFICE
CERTIFICATE OF CORRECTION

PATENT NO. : 4,856,321

DATED : August 15, 1989

INVENTOR(S) : Jack W. Smalling, et. al.

It is certified that error appears in the above-identified patent and that said Letters Patent is hereby corrected as shown below:

Column 21, line 66 delete "transmit" and insert--transit--.

Column 23, line 38 delete "measing" and insert--measuring--.

Signed and Sealed this

Fifteenth Day of December, 1992

Attest:

DOUGLAS B. COMER

*Attesting Officer*     *Acting Commissioner of Patents and Trademarks*